United States Patent [19]

Baker et al.

[11] Patent Number: 5,344,990
[45] Date of Patent: Sep. 6, 1994

[54] PROCESS FOR THE PREPARATION OF A RENIN INHIBITING COMPOUND

[75] Inventors: William R. Baker, Libertyville, Ill.; Stephen L. Condon, Kenosha, Wis.

[73] Assignee: Abbott Laboratories, Abbott Park, Ill.

[21] Appl. No.: 131,837

[22] Filed: Oct. 5, 1993

Related U.S. Application Data

[60] Division of Ser. No. 15,873, Feb. 10, 1993, Pat. No. 5,275,950, which is a continuation of Ser. No. 777,887, Oct. 15, 1991, abandoned, which is a continuation-in-part of Ser. No. 716,028, Jun. 14, 1991, abandoned, which is a continuation-in-part of Ser. No. 683,663, Apr. 15, 1991, which is a continuation-in-part of Ser. No. 564,925, Aug. 9, 1990, abandoned, which is a continuation-in-part of Ser. No. 522,349, May 11, 1990, abandoned.

[51] Int. Cl.$^5$ .................. C07C 209/00; C07C 317/00
[52] U.S. Cl. .................... 564/487; 514/252; 544/369; 564/355; 564/356; 564/357; 564/413; 564/445; 564/446; 564/450; 564/453; 564/507; 549/451
[58] Field of Search ............. 549/451; 564/445, 446, 564/450, 453, 487, 355–357, 507, 413

[56] References Cited

U.S. PATENT DOCUMENTS 4,845,079 7/1989 Luly et al. .................... 514/18

OTHER PUBLICATIONS

Bose et al., CA 102:220618x (1985).
Deshong et al., CA 102:167035b (1984).
Deshong et al., CA 101:131016m (1984).
Fronza et al., CA 100:175169x (1983).
Fuganti et al., CA 98:143762j (1983).
Deshong et al., CA 98:126525s (1983).
Fronza et al., CA 96:200056s (1981).
Baker et al., CA 119:9157q (1993).
Baker et al., CA 116:236150p (1992).
Brandi et al., CA 116:59498k (1991).
Kita et al., CA 112:99059s (1989).
Taguchi et al., CA 110:193270j (1988).
Fronza et al., CA 109:190714a (1988).
Tamura et al., CA 109:149792m (1988).
Kita et al., CA 107(25):237181a (1987).
Luly, et al., J. Org. Chem., 53, 6109 (1988).
Luly, et al., J. Med. Chem., 31, 2264 (1988).
Wood, et al., Tetrahedron Letters, 31, 6329 (1990).
Taguchi, et al., Tetrahedron Letters, 29, 5291 (1988).

*Primary Examiner*—Cecilia Tsang
*Attorney, Agent, or Firm*—Steven R. Crowley

[57] ABSTRACT

Intermediates and a process for their preparation are disclosed which are useful for the preparation of a renin inhibiting compound of the formula:

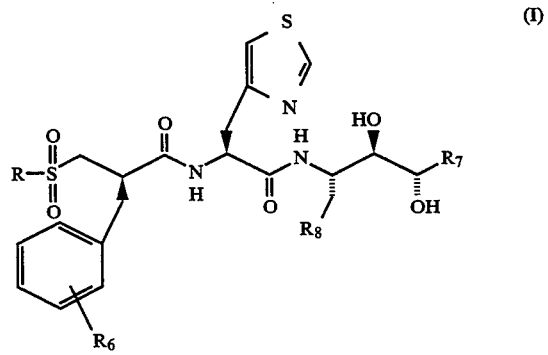

(I)

wherein R is a nitrogen-containing heterocycle which is bonded via a nitrogen atom to the sulfonyl group, $R_6$ is hydrogen, alkoxy, halogen or loweralkyl, $R_7$ is loweralkyl having 2 to 7 carbon atoms, and $R_8$ is loweralkyl, cycloalkyl, or aryl or a pharmaceutically acceptable acid addition salt thereof.

9 Claims, No Drawings

PROCESS FOR THE PREPARATION OF A RENIN INHIBITING COMPOUND

This is a division of U.S. patent application Ser. No. 08/015,873, filed Feb. 10, 1993, U.S. Pat. No. 5,275,950 which is a continuation of U.S. patent application Ser. No. 07/777,887, filed Oct. 15, 1991, now abandoned, which is a continuation-in-part of U.S. Pat. application Ser. No. 716,028, filed Jun. 14, 1991, now abandoned which is a continuation-in-part of U.S. patent application Ser. No. 683,663, filed Apr. 15, 1991, which is a continuation-in-part of U.S. patent application Ser. No. 564,925, filed Aug. 9, 1990, now abandoned, which is a continuation-in-part of U.S. patent application Ser. No. 522,349, filed May 11, 1990, now abandoned.

TECHNICAL FIELD

A process is disclosed for the preparation of a renin inhibiting compound and intermediates which are useful in the process.

BACKGROUND OF THE INVENTION

Compounds which inhibit the enzyme renin have been the subject of much research in recent years. Renin inhibitors are designed to mimic the peptide substrate of renin and, therefore, are peptide-like in their structure. However, in order to improve the biopharmaceutical properties of renin inhibitors, the compounds must be as non-peptide-like as possible. A renin inhibiting compound which has been found to be of particular interest is the compound of the formula:

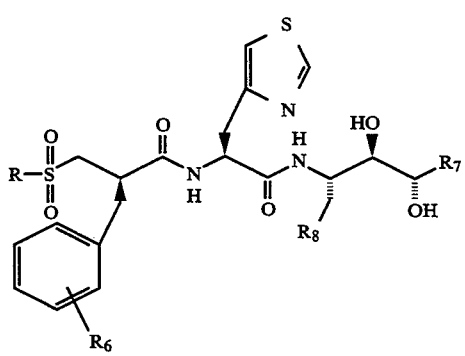

(I)

wherein R is a nitrogen-containing heterocycle which is bonded via a nitrogen atom to the sulfonyl group, $R_6$ is hydrogen, alkoxy, halogen or loweralkyl, $R_7$ is loweralkyl having 2 to 7 carbon atoms, and $R_8$ is loweralkyl, cycloalkyl, or aryl or a pharmaceutically acceptable acid addition salt thereof. A heterocycle of particular interest is 1-methylpiperazin-4-yl.

A renin inhibiting compound of most interest is the compound of formula Ia:

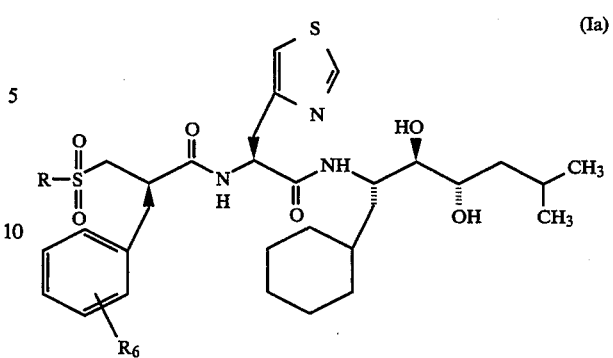

(Ia)

wherein R and $R_6$ are defined as above or a pharmaceutically acceptable acid addition salt thereof.

Unlike a peptide, compound I is not composed of readily available amino acids. Therefore, methods are needed for the preparation of intermediates which are useful for the preparation of compounds such as I.

DISCLOSURE OF THE INVENTION

In accordance with the present invention, there is disclosed a process for the preparation of I as well as intermediates useful for the preparation of compound I. In particular, the present invention relates to processes for the preparation of a substantially pure compound II ($R_{1a}$ and $R_{1b}$ are independently selected from hydrogen and an N-protecting group) or an acid addition salt thereof, a substantially pure compound III (R is a nitrogen-containing heterocycle which is bonded through a nitrogen atom to the sulfonyl group and $R_6$ is hydrogen, alkoxy, halogen or loweralkyl) or an acid addition salt thereof and a substantially pure compound IV ($R_7$ is loweralkyl having 2 to 7 carbon atoms and $R_8$ is loweralkyl, cycloalkyl or aryl) or an acid addition salt thereof.

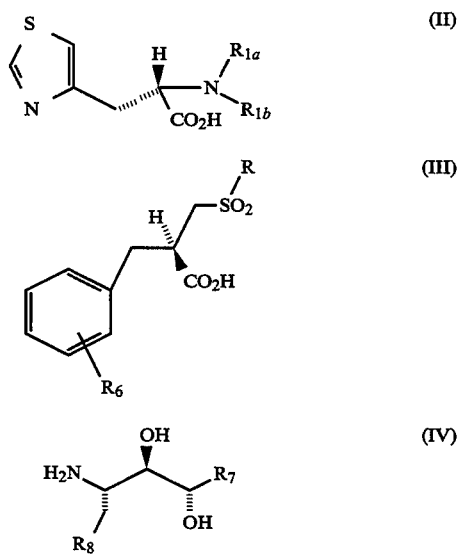

A process for the preparation of substantially pure II is outlined in Scheme 1. A mixture of malonate 1 ($R_2$ is alkanoyl and $R_3$ and $R_4$ are independently selected from loweralkyl and benzyl) and 2 ($X_1$ and $X_2$ are independently selected from halogen, for example, Br, alkoxy, for example, methoxy, ethoxy, or benzyloxy, and trimethylsilyloxy) in an inert solvent (for example, tetrahydrofuran (THF), dimethoxyethane (DME), ethanol or dimethylformamide (DMF) and the like) at a temperature of from about 0° C. to about 100° C. is treated with a base (for example, NaH, KH or sodium ethoxide and the like) to give 3. Reaction of 3 with a halogenating agent (for example, N-bromosuccinimide, N-chlorosuccinimide, bromine or chlorine and the like) in a mixture of water and a water miscible solvent (for example, acetonitrile/H$_2$O or ethanol/H$_2$O and the like) at a temperature of from about −2° C. to about 30° C. provides 4 ($X_3$ is bromo or chloro). Reaction of 4 with thioformamide in an inert solvent (for example, THF or acetone and the like) at a temperature of from about 0° C. to about 65° C. gives thiazole 5. Alternatively, malonate 1 can be reacted with thiazole 6 ($X_4$ is Br, Cl or I) to give thiazole 5.

Hydrolysis of 5 by treatment with aqueous base (for example, LiOH, KOH, NaOH and the like) in a mixture of water and a water miscible solvent (for example, THF/ethanol/H$_2$O and the like) at a temperature of from about 0° C. to about 25° C. provides the intermediate monoacid ($R_4$ is hydrogen). Decarboxylation to give 7 is accomplished by refluxing a solution of the monoacid in dioxane or toluene and the like. Racemic 7 in an aqueous solution at a pH of from about 6.5 to about 7.5 is treated with an esterase (for example, Subtilisin Carlsberg or chymotrypsin and the like) at a temperature of from about 20° C. to about 40° C. to provide a mixture of 8 and 9. Extraction of an aqueous mixture of 8 and 9 at a pH of from about 7 to about 8 with an organic solvent (for example, chloroform, dichloromethane or ethyl acetate and the like) separates 8 from 9. Acidification of the aqueous layer provides 9.

Ester 8 can be recycled by racemization under basic conditions (for example, sodium ethoxide/ethanol and the like at a temperature of from about 0° C. to about the reflux temperature of the solvent being used) to provide racemic 7, which can be subjected to the resolution conditions outlined above.

Acidic hydrolysis (for example, aqueous 6N HCl at a temperature of from about 25° C. to about 100° C.) provides the thiazolylalanine acid addition salt 10. Protection of the alpha-amino group (for example, by treatment of 10 at a pH of from about 8 to about 11 in an inert solvent, for example, THF or dioxane and the like at a temperature of from about 25° C. to about 50° C.) with, for example, di-t-butyldicarbonate, benzylchloroformate, an alkanoyl halide and the like provides II ($R_{1a}$ is an N-protecting group, for example, t-butyloxycarbonyl and the like and $R_{1b}$ is hydrogen).

An alternative process for the preparation of II is Outlined in Scheme 2. Compound 3 is decarboalkoxylated (for example, by treatment with sodium chloride or lithium bromide and the like in an inert solvent such as dimethylformamide or dimethylsulfoxide and the like at a temperature of from about 145° C. to about 180° C.) to provide 11. Enzymatic ester hydrolysis of the L-isomer of 11 (for example, by treatment with an esterase such as Subtilisin Carlsberg or chymotrypsin in an aqueous solution at a pH of from about 6.9 to about 7.1 and a temperature of from about 25° C. to about 40° C.), followed by separation of the D-isomer of 11 by organic extraction, provides the L-carboxylic acid derivative of 11. Enzymatic hydrolysis of the amide (for example, by treatment with an acylase such as Acylase I from Aspergillus species or Acylase I from porcine kidney in an aqueous solution at a pH of from about 6 to about 8 and a temperature of from about 2° C. to about 40° C.), provides the intermediate L-amino acid derivative of 11. Protection of the alpha-amino group (for example, by treatment of the L-amino acid derivative of 11 at a pH of from about 9 to about 10 in an inert solvent, for example, THF, methylene chloride or dioxane and the like at a temperature of from about 20° C. to 40° C. with, for example, di-t-butyldicarbonate, benzyl chloroformate or an alkanoyl halide and the like provides the N-protected L-amino acid derivative of 11. Lastly, reaction of the N-protected L-amino acid derivative of 11 with a halogenating agent (for example, N-bromosuccinimide, N-chlorosuccinimide, bromine or chlorine and the like) in a mixture of water and a water miscible solvent (for example, acetonitrile/H$_2$O, THF/H$_2$O, ethanol/H$_2$O or methanol/H$_2$O and the like) at a temperature of from about 0° C. to about 25° C. provides 12 ($X_3$ is bromo or chloro, $R_{1a}$ is an N-protecting group for example, t-butyloxycarbonyl). Reaction of 12 with thioformamide in an inert solvent (for example, THF or acetone and the like) at a temperature of from about 0° C. to about 40° C. gives II ($R_{1a}$ is an N-protecting group for example, t-butyloxycarbonyl and $R_{1b}$ is hydrogen).

An alternative process for the preparation of racemic intermediate 7 is outlined in Scheme 3. A mixture of malonate 1 ($R_2$ is alkanoyl and $R_3$ and $R_4$ are independently selected from loweralkyl and benzyl) and 2 ($X_1$ and $X_2$ are independently selected from halogen, for example chlorine, alkoxy, for example, methoxy, ethoxy, or benzyloxy, and trimethylsilyloxy) in an inert solvent (for example, tetrahydrofuran (THF), dimethoxyethane (DME), ethanol or dimethyformamide (DMF) and the like) at a temperature of from about 0° C. to about 100° C. is treated with a base (for example, sodium hydride, potassium hydride or sodium tert-butoxide and the like). The excess base is neutralized (for example, with hydrochloric acid) and then treated with a soluble bromide salt such as lithium bromide at a temperature of from about 0° C. to about 100° C. to afford the non-isolated intermediate 13. The solvent is removed under reduced pressure, and 13 is reacted with a halogenating agent (for example, N-bromosuccinimide, N-chlorosuccinimide, bromine or chlorine and the like) in a mixture of water and a water miscible solvent (for example, acetonitrile/water or ethanol/water and the like) at a temperature of from about −2° C. to about 30° C. to provide 14 ($X_3$ is bromo or chloro). Reaction of 14 with potassium thiocyanate in glacial acetic acid, followed by hydrobromic acid at a temperature of from about −2° C. to about 30° C., affords bromothiazole 15. Conventional debromination methodology (for example, zinc in acetic acid) affords compound 7. Alternatively, bromoketone 14 can be reacted with thioformamide in an inert solvent (for example, THF or acetone and the like) at a temperature of from about 0° C. to about 65° C. to give thiazole 7. This compound can be converted to compound II by the procedures described in Scheme 1.

A process for the preparation of substantially pure III is outlined in Scheme 4. Reaction of 16 ($R_5$ is loweralkyl, $X_4$ is a halogen and $R_6$ is hydrogen, alkoxy, hologen or loweralkyl) with Na$_2$SO$_3$ in a solvent such as aqueous methanol or ethanol and the like at a temperature of from about 35° C. to about 65° C. followed by olefin reduction (for example, with Raney nickel and hydrogen or hydrogen and rhodium and the like in a solvent such as methanol/H$_2$O or ethanol/H$_2$O at a temperature of from about 25° C. to about 70° C.) provides 17.

Alternatively, 17 can be prepared by reaction of 16a with NaHSO$_3$.

Formation of the sulfonyl chloride derivative of 17 (for example, by treatment with a chlorinating agent such as PCl$_5$ or POCl$_3$ and the like in an inert solvent such as toluene or heptane and the like at a temperature of from about 25° C. to about 70° C.), followed by reaction with a nitrogen-containing heterocycle (for example, morpholine, piperazine, N-methylpiperazine and the like) in an inert solvent (such as dichloromethane and the like) at a temperature of from about 0° C. to about 25° C. provides 18. Selective ester hydrolysis of the L-isomer of 18 (for example, by treatment with an esterase such as Subtilisin Carlsberg or chymotrypsin and the like in an aqueous solvent such as 25% acetone/H$_2$O and the like at a pH of from about 7.5 to about 8.0 at about ambient temperature) provides a mixture of the D-isomer of 18 and III. This mixture can be separated by extraction to provide III.

Scheme 5 illustrates a synthesis of IV. D-Isoascorbic acid 19 is converted to the known lactone 20 (Cohen, N., et al.; J. Am. Chem. Soc. 105, 3661 (1983)). Treatment of 20 with a metal hydride reducing agent (for example diisobutylaluminum hydride and the like) affords lactol 21 (Cohen and co-workers; J. Am. Chem. Soc. 105, 3661 (1983)). Reaction of lactol 21 with a phosphorane (Ph$_3$P=C(R$_{7a1}$) (R$_{7a2}$) wherein R$_{7a1}$ and R$_{7a2}$ are independently selected from hydrogen and loweralkyl, for example, Ph$_3$P=C (CH$_3$)$_2$), prepared by treating the alkyl triphenylphosphonium bromide or iodide with a base (for example, butyllithium, potassium bis (trimethylsilylamide, and the like), at a temperature of from about 0° C. to about −78° C. in an inert solvent (for example, tetrahydrofuran (THF), dimethoxyethane (DME), dioxane and the like) provides alcohol 22 (R$_{7a}$=—CH=C(R$_{7a1}$) (R$_{7a2}$), for example, —CH=C(CH$_3$)$_2$). Catalytic hydrogenation (for example, using a palladium on carbon catalyst) affords the dihydro compound 23. Oxidation (for example, using Swern conditions or NaOCl, TEMPO (4-methoxy-2,2,6,6-tetramethylpiperidin-1-oxide), and the like) of either alcohol 22 or 23 affords aldehyde 24a or 24b, respectively. Reaction of 24a or 24b with an arylalkylamine (for example, benzylamine or a substituted benzylamine (p-MeO or p-NO$_2$) and the like) in an anhydrous solvent (for example, toluene, THF, Et$_2$O, CH$_2$Cl$_2$ and the like) provides the corresponding imine 25a or 25b, respectively. Similarly, reaction of 24a or 24b with a dialkylhydrazine (for example, N,N-dimethylhydrazine and the like) in an anhydrous solvent (for example, CH$_2$Cl$_2$, THF, Et$_2$O and the like) provides the corresponding hydrazone 25c or 25d, respectively.

Reaction of 25a, 25b, 25c, or 25d with an organometallic reagent R$_8$CH$_2$M wherein R$_8$ is loweralkyl, cycloalkyl or aryl and M is a metal (for example, lithium or a magnesium halide such as magnesium bromide; and the like, for example, cyclohexylmethyllithium, cyclohexylmethylmagnesium bromide/CeCl$_3$, benzylmagnesium bromide and the like) provides 26a, 26b, 26c, or 26d, respectively. In an preferred embodiment, 25a, 25b, 25c, or 25d is reacted with cyclohexylmethyllithium in an inert solvent (for example, diethyl ether, pentane/diethyl ether (3:2), and the like) at a temperature of from about −30° C. to about ambient temperature to provide 26a, 26b, 26c, or 26d, respectively.

Catalytic hydrogenation of 26a, 26b, 26c, or 26d (for example, using Raney nickel catalyst, PtO$_2$ in HOAc, Pd/C in HCl, and the like), followed by deprotection of the acetonide (for example, using HCl/MeOH) provides IV.

An alternative synthesis of hydrazone 25d is illustrated in Scheme 6. The known alcohol 28 (Schreiber, S. L. and co-workers, J. Am. Chem. Soc. 1987, 109, 1525) is reacted with isopropylmagnesium chloride in the presence of a catalyst such as cuprous iodide to give alcohol 29. Treatment of 29 with an acid (such as p-toluenesulfonic acid) and 2,2-dimethoxypropane gives the acetonide 30. Oxidative cleavage of the double bond with ozone and reduction of the ozonide with Zn/HOAc, affords the aldehyde 24b. Reaction of 24b with dimethylhydrazine as previously described gives the hydrazone 25d. This compound can be elaborated by the procedures described in Scheme 5 to give the amino diol IV.

Alternate syntheses of compounds 22a, 24a, and IV are shown in Scheme 7. Wittig olefination of the known acetonide lactone 38 (Hudlicky, T.; Price, J. D.; Synlett. 159 (1990)) affords the acid 32. The acid 32 is reduced using, for example, isobutylchloroformate/sodium borohydride (according to the procedure of Rodriguez et al. Tetrahedron Letter 32, 923–26 (1991)) to give alcohol 22a. Aldehyde 24a can be prepared from acid 32 by conversion to an imide, for example, using methoxymethylamine and isobutylchloroformate, followed by reduction using, for example, lithium aluminum hydride. Compounds 22a and 24a can be elaborated by the procedures described in Scheme 5 to give amino diol IV. Intermediate 32 can also be reacted with either two equivalents of R$_8$CH$_2$Li (for example, benzyllithium or cyclohexylmethyllithium) to give ketone 33a. Alternatively, catalytic hydrogenation of 32, followed by reaction with two equivalents of R$_8$CH$_2$Li, provides 33b. Reaction of 33a or 33b with hydroxylamine, followed by hydrogenation and deprotection of the acetonide, gives IV. Alternatively, reaction of 33a or 33b with ammonium acetate and sodium cyanoborohydride, followed by hydrogenation (33a) and deprotection of the acetonide, gives IV.

An alternate synthesis of intermediate 24b is illustrated in Scheme 8. Payne rearrangement of the known optically active epoxy alcohol 34 (Smith et al. Tetrahedron Lett. 31, 6329 (1990)) affords the diol sulfide which is protected as the acetonide 35. Oxidation of 35 to the sulfoxide using, for example, m-chloroperoxybenzoic acid, followed by Pummerer rearrangement (Ac$_2$O, heat), and then hydrolysis, gives the aldehyde 24b. This compound can be elaborated by the procedures described in Scheme 7 to give the amino diol IV.

Scheme 9 outlines an alternative preparation of amino diol IV (R$_7$=CH$_2$CH (CH$_3$)$_2$) (R$_8$=cyclohexyl). Starting from either diphenylmethane or cyclohexylmethylbenzene, microbial oxidation using *Pseudomonas putida*, followed by hydroxyl protection either as a diacetate or acetonide, affords the protected diols 37a-d. Ozonolysis of the diene, followed by selective Wittig olefination of the resulting keto aldehyde, affords ketone 38a-d. Compound 38a-d is reacted with hydroxylamine, reduced, for example, by catalytic hydrogenation, and the hydroxy-protecting groups removed to afford amino diol IV.

Scheme 10 outlines the preparation of I from intermediates II, III and IV. Amino acid II (R$_{1a}$ is an N-protecting group) or an activated acid derivative thereof, is coupled with amino diol IV using standard peptide coupling methods. Removal of the protecting group R$_{1a}$ from the resulting product provides 39. Amine 39 is then coupled with carboxylic acid III, or an activated acid derivative thereof, using standard peptide coupling methods to provide I.

Alternatively, carboxylic acid III, or an activated acid derivative thereof, can be coupled with 40. Removal of the $R_4$ group from the resulting product by hydrolysis or hydrogenation provides 41. Carboxylic acid 41, or an activated acid derivative thereof, can then be coupled with IV to provide I.

Activated derivatives of carboxylic acids as mentioned herein include acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

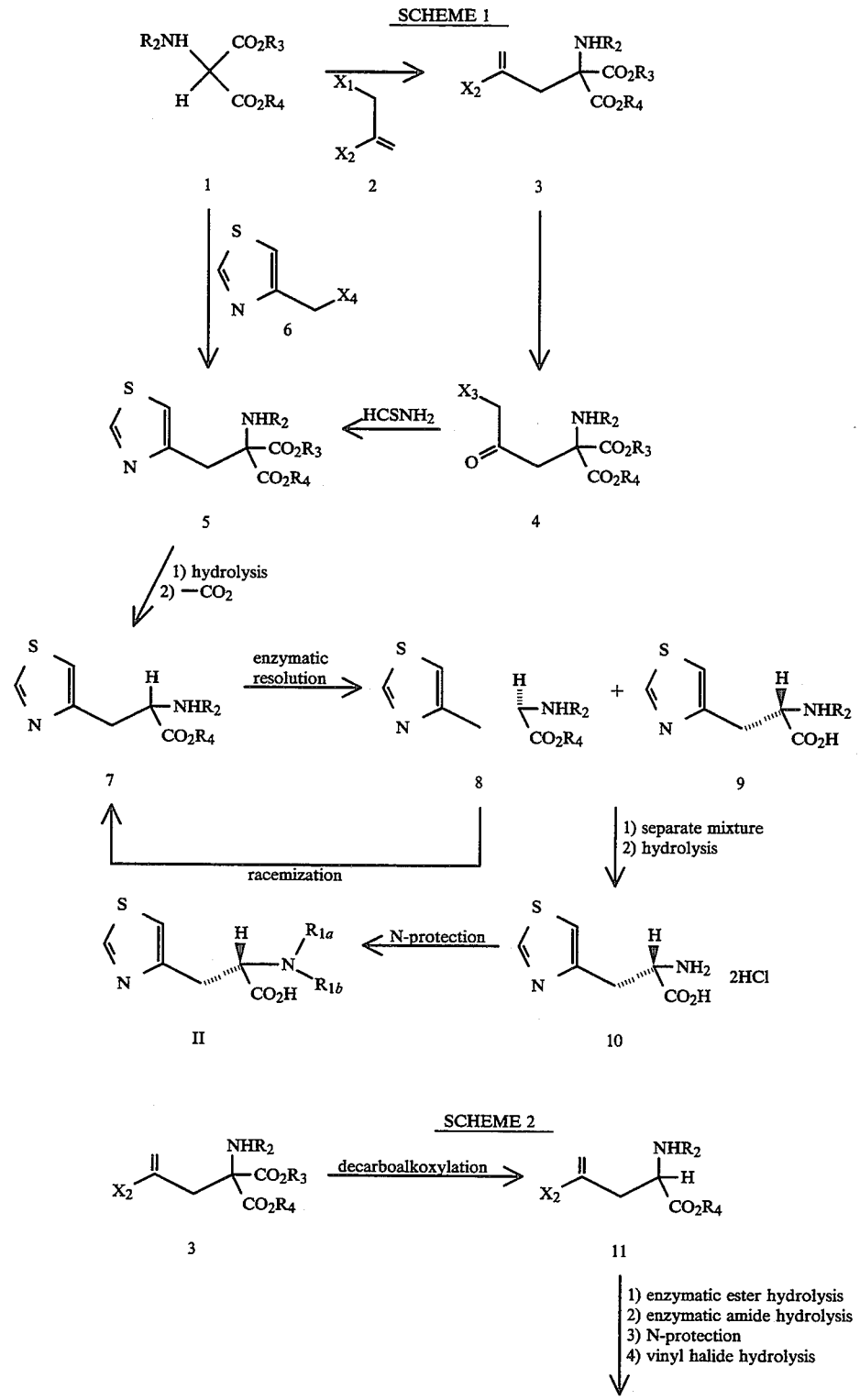

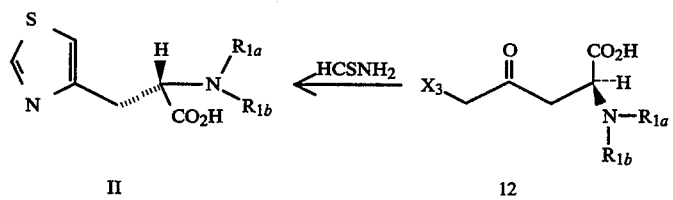
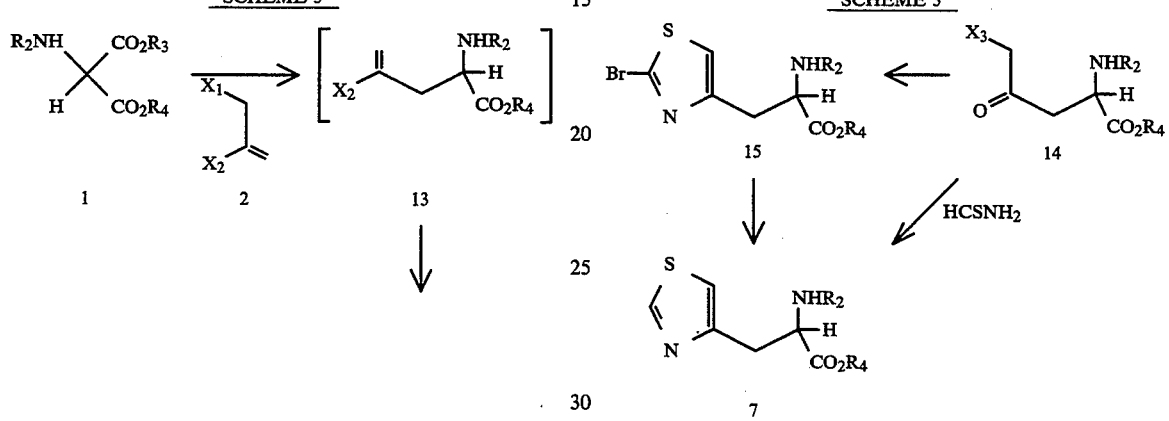
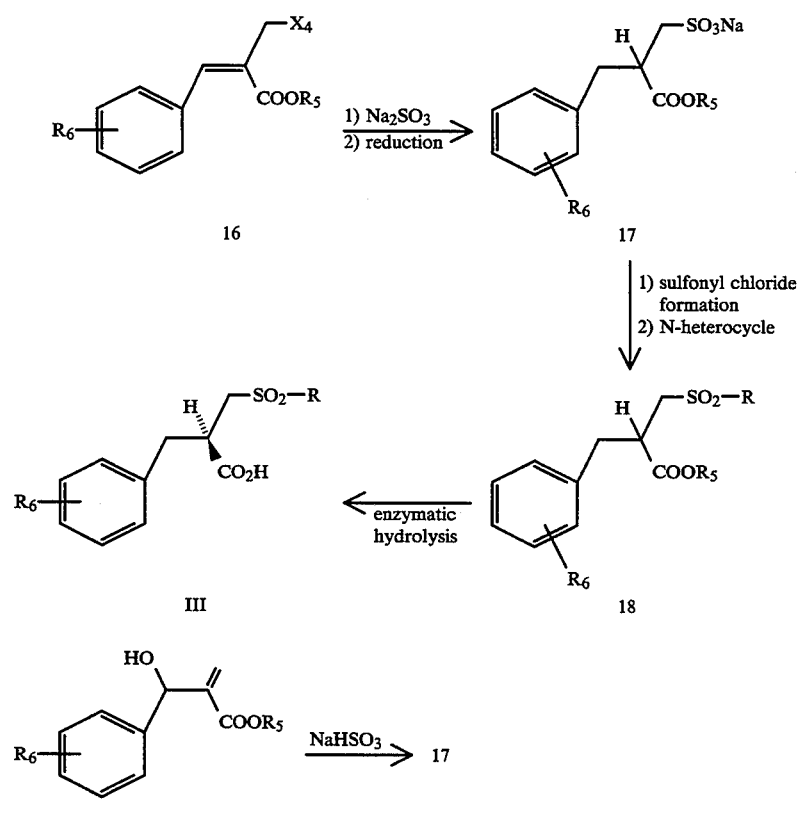

SCHEME 5
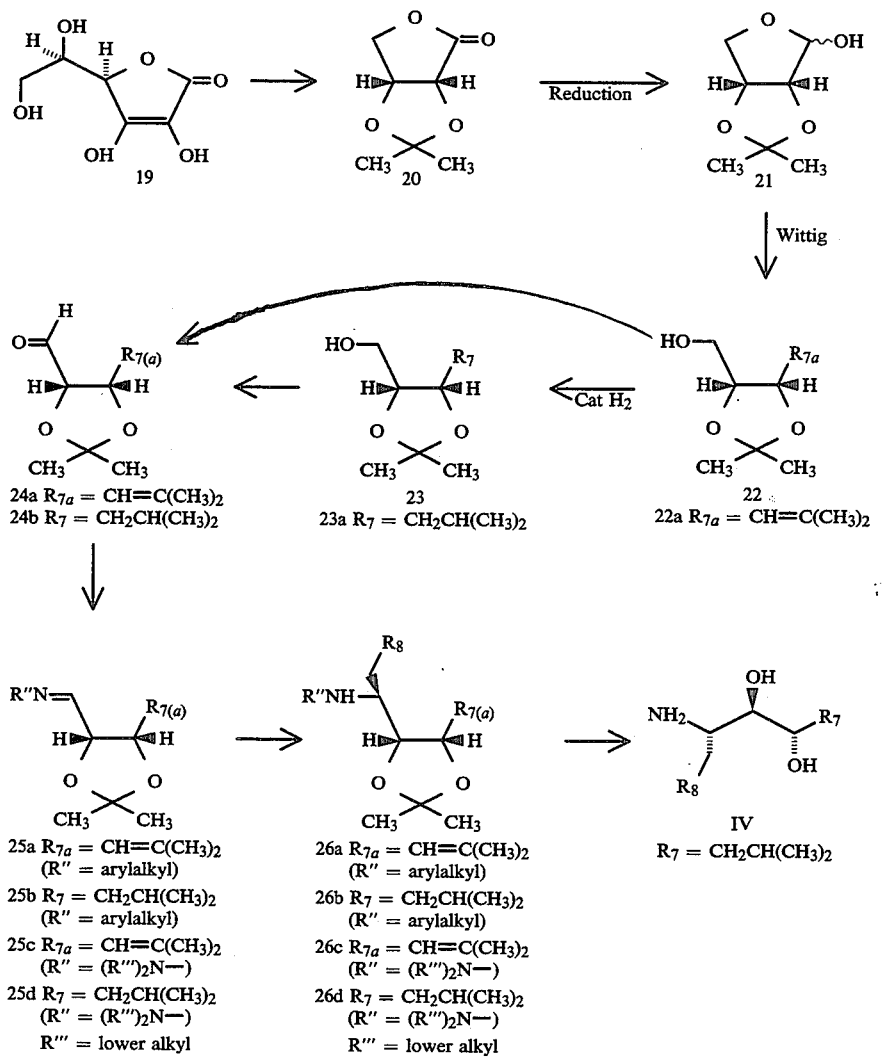
SCHEME 6
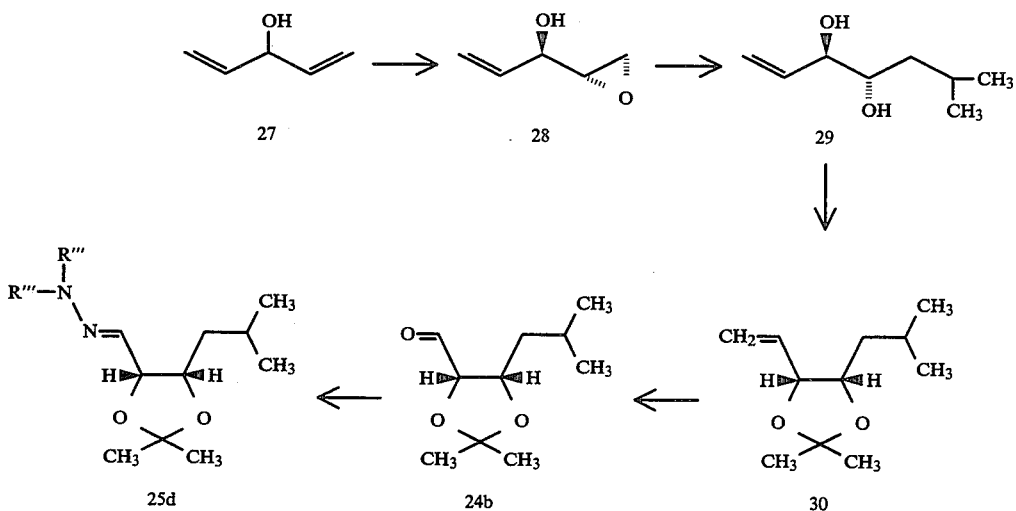

5,344,990
13 14
SCHEME 7
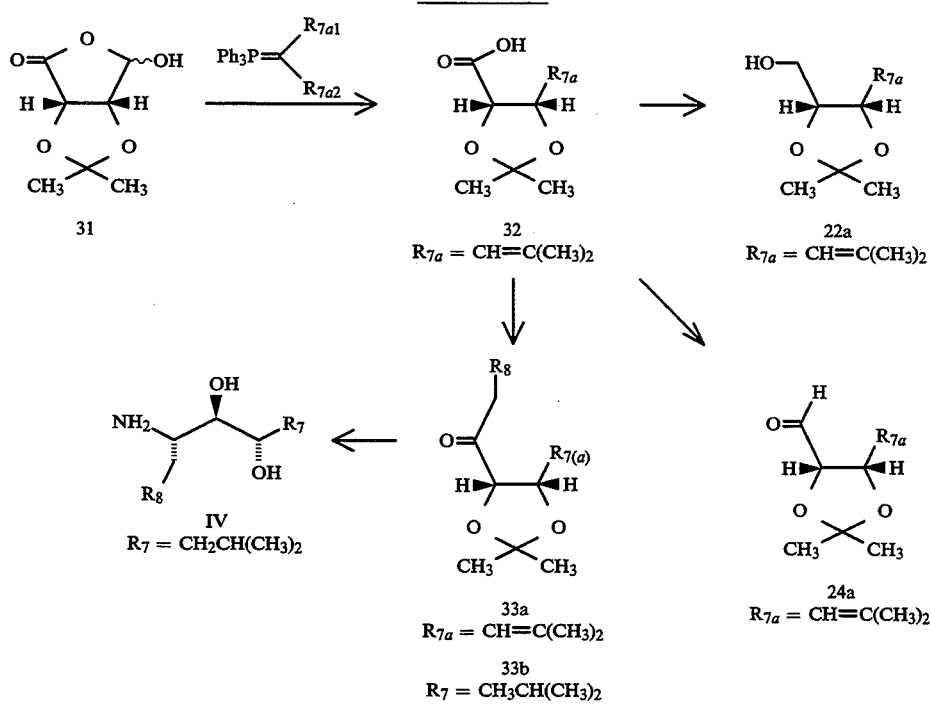
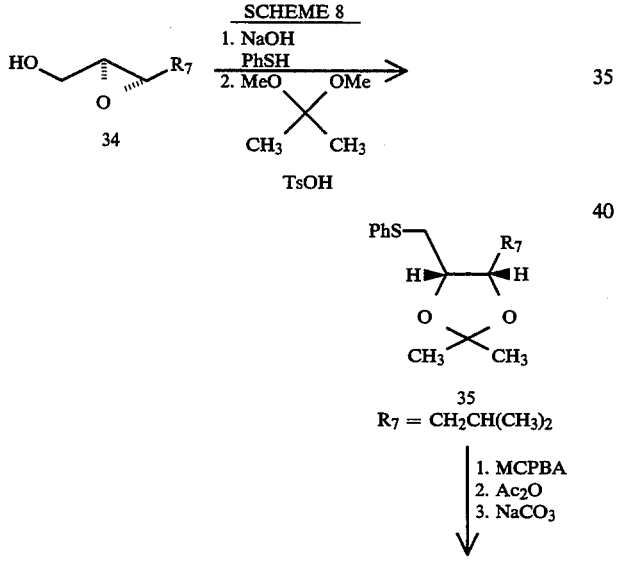
SCHEME 8
-continued
SCHEME 8
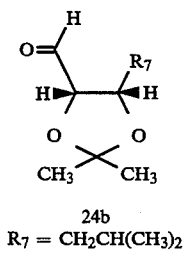
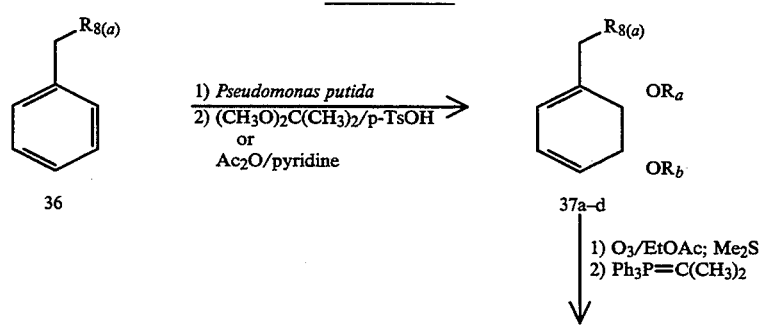

SCHEME 9
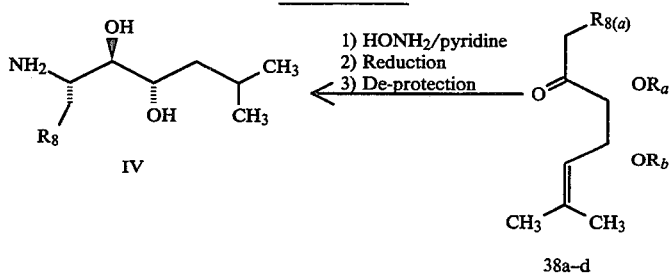
a  $R_{8a} = Ph; R_a, R_b = C(CH_3)_2$
b  $R_8 = c\text{-}C_6H_{11}; R_a, R_b = C(CH_3)_2$
c  $R_{8a} = Ph; R_a = R_b = Ac$
d  $R_8 = c\text{-}C_6H_{11}; R_a = R_b = Ac$
SCHEME 10
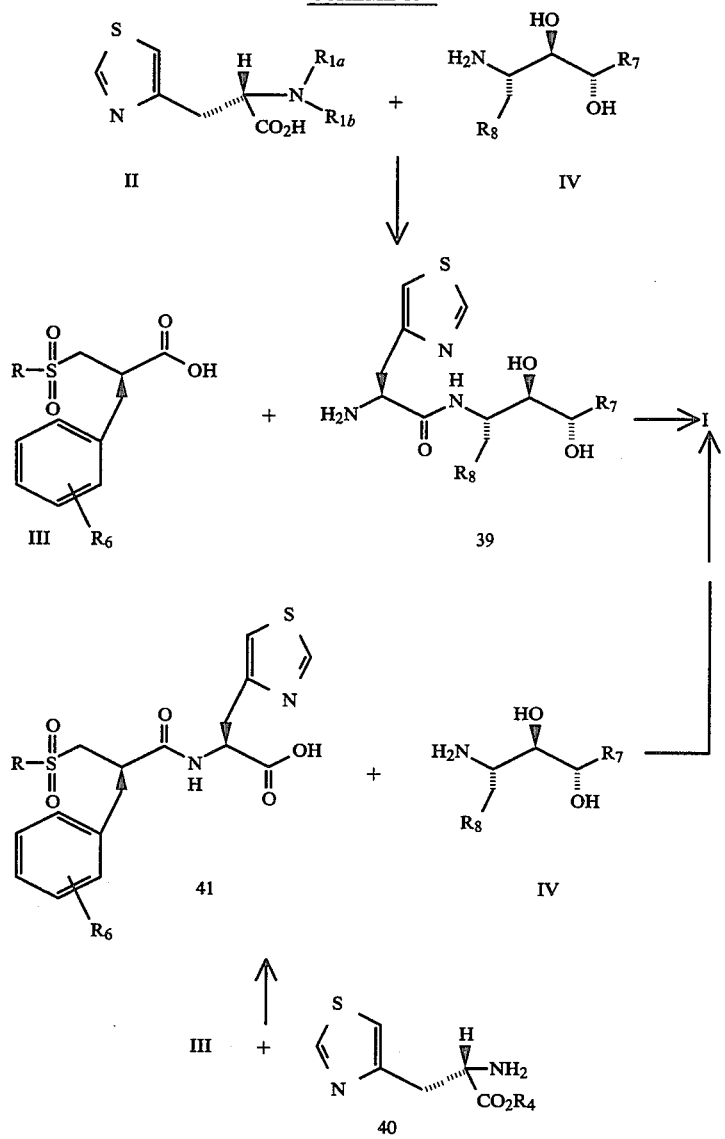
The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one or two substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "alkylene" as used herein refers to a straight or branched chain carbon diradical containing from 1 to 7 carbon atoms including, but not limited to, —$CH_2$—, —$CH_2CH_2$—, —CH($CH_3$)$CH_2$—, —$CH_2CH_2CH_2$— and the like.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The term "alkanoyl" as used herein refers to $R_{15}C(O)$— wherein $R_{15}$ is a loweralkyl group.

The term "alkanoyl halide" as used herein refers to $R_{15}C(O)$—X wherein X is halogen and $R_{15}$ is a loweralkyl group.

The terms "alkoxy" and "thioalkoxy" as used herein refer to $R_{16}O$— and $R_{16}S$—, respectively, wherein $R_{16}$ is a loweralkyl group or benzyl.

The term "halo" or "halogen" as used herein refers to —Cl, —Br, —I or —F.

The term "alkylamino" as used herein refers to —$NHR_{12}$ wherein $R_{12}$ is a loweralkyl group.

The term "dialkylamino" as used herein refers to —$NR_{13}R_{14}$ wherein $R_{13}$ and $R_{14}$ are independently selected from loweralkyl groups.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "arylalkyl" as used herein refers to a loweralkyl radical to which is appended an aryl group including, but not limited to, benzyl, 4-hydroxybenzyl, 1-naphthylmethyl and the like.

The term "alkoxyalkoxy" as used herein refers to $R_9OR_{10}O$— wherein $R_9$ is a loweralkyl group and $R_{10}$ is an alkylene group including, but not limited to, methoxymethoxy, ethoxymethoxy and the like.

The term "polyalkoxy" as used herein refers to —$OR_{11}$ wherein $R_{11}$ is a straight or branched chain containing 2–5, $C_{n'}$—O—$C_{n''}$ linkages wherein n' and n" are independently selected from 1 to 3 including, but not limited to, methoxyethoxymethoxy and the like.

The term "alkoxycarbonyl" as used herein refers to $R_{17}C(O)$— wherein $R_{17}$ is an alkoxy group.

The term "nitrogen-containing heterocycle" as used herein refers to a saturated or partially unsaturated 5- or 6-membered ring containing 1, 2 or 3 nitrogen atoms; 1 nitrogen atom and 1 sulfur atom; or 1 nitrogen atom and 1 oxygen atom. The nitrogen-containing heterocycle can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, polyalkoxy, haloalkyl, cycloalkyl, aryl, arylalkyl, —COOH, —$SO_3H$ and loweralkyl. In addition, a nitrogen-containing heterocycle having more than one nitrogen atom can be N-protected. The nitrogen-containing heterocycles are bonded to the rest of the molecule through a nitrogen atom. Representative nitrogen-containing heterocycles are azetidinyl, pyrrolidinyl, piperidinyl, piperazinyl, N-methylpiperazinyl, morpholinyl or thiomorpholinyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, t-butyloxycarbonyl (Boc), benzyloxycarbonyl (Cbz) and the like.

The terms "pharmaceutically acceptable salt" and "acid addition salt" as used herein refer to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate and the like.

Examples of acid which can be employed to form pharmaceutically acceptable acid addition salts include such inorgnic acids as hydrochloric acid, sulphuric acid and phosphoric acid and such organic acids as oxalic acid, maleic acid, succinic acid and citric acid.

The term "substantially pure" as used herein refers to a compound which is contaminated by not more than 5% of its enantiomer or diastereomer and preferably by not more than 1% of its enantiomer or diastereomer.

The following Examples will serve to further illustrate the processes of the present invention.

EXAMPLE 1

(2S)-2-Benzyl-3-(1-methyl-piperazin-4-ylsulfonyl)propionyl-(L)-4-Thiazolyl)Ala Amide of (2S,3R,4S)-2-Amino-1-cyclohexyl-3,4-dihydroxy-6-methylheptane

Example 1A

Methyl 3-Hydroxy-2-methylene-3-phenylpropionate

A mixture of benzaldehyde (82.1 mL, 0.81 mol), methyl acrylate (109.1 mL, 1.211 mol), 1,4-diazabicyclo (2,2,2)octane (13.6 g, 0.12 mol), and acetic acid (1.4 mL, 0.024 mol) was allowed to stir at 35° C. for 60 hours, at which point the reaction was determined to have proceeded to 70% completion by $^1H$ NMR. Methyl acrylate (20.9 mL, 0.23 mol) was then added and the solution was allowed to react at 35° C. for an additional 48 hours. The mixture was diluted with diethyl ether (1.0 L) and washed with 2×200 mL portions of a pH 7 phosphate buffer. After concentration in vacuo, the remaining mixture was distilled at reduced pressure (12 mm) to afford 6.5 g of unreacted benzaldehyde and 130.0 g (90%) of the desired product as a colorless oil: b.p. 130° C. (12 mm); IR (film) 1718, 1440 cm$^{-1}$; $^1$H NMR (CDCl$_3$, 300 MHz) δ 3.67 (s, 3H), 5.52 (br s, 1H), 5.83–5.85 (m, 1H), 6.29–6.31 (m, 1H), 7.23–7.39 (m, 5H); $^{13}$C NMR (75 MHz, CDCl$_3$) δ 51.8, 72.9, 125.8, 126.5, 127.7, 128.3, 141.2, 141.9, 166.6.

Example 1B (Z)-1-Bromo-2-carbomethoxy-3-phenyl-2-propene

To a 2 L, 3-neck Morton flask fitted with a thermometer, a mechanical stirrer, and an addition funnel was added the resultant compound from Example 1B (305.9 g, 1.585 mol) followed by addition of 48% hydrobromic acid (505 mL, 4.46 mol) in one portion. The flask was immersed in an ice-water bath, at which time concentrated sulfuric acid (460 mL, 8.62 mol) was added dropwise over 90 minutes and the internal temperature of the reaction mixture was maintained at 23°–27° C. throughout the addition process. After removal of the ice-water bath, the mixture was allowed to stir at ambient temperature overnight. The solution was then transferred to a separatory funnel and the organic layer was allowed to separate from the acid layer. The acids were drained and the organic layer was diluted with 2 L of a 1:1 ethyl acetate/hexane solution, washed with saturated aqueous sodium bicarbonate solution (1 L), dried over sodium sulfate, and concentrated to yield 400 g (99%) of the desired product as a light yellow oil, which was used without any additional purification: b.p. 180° C. (12 mm); IR (film) 1718, 712 cm$^{-1}$; $^1$H NMR (CDCl$_3$, 300 MHz) δ 3.89 (s, 3H), 4.40 (s, 2H), 7.38–7.45 (m, 3H), 7.56–7.60 (m, 2H), 7.83 (s, 1H); $^{13}$C NMR (75 MHz, CDCl$_3$) δ 26.77, 52.47, 128.63, 128.87, 129.61, 134.20, 142.95, 166.62.

Example 1C (Z)-2-Carbomethoxy-3-phenyl-2-propene-1-sulfonic Acid Sodium Salt To a 12 L, 3-neck round bottom flask fitted with a mechanical stirrer, thermometer and an addition funnel was added the resultant product from Example 1B (400 g, 1.57 mol) and methanol (4 L). The mixture was warmed to 50° C. and a solution of sodium sulfite (199 g, 1.57 mol) dissolved in water (4 L) was added over 75 min while the internal temperature of the flask was maintained at 50° C. After the addition was complete, the clear solution was allowed to stir at 50° C. for an additional 45 minutes. The reaction mixture in solution was taken to the next step without additional purification. The compound may be isolated by concentration to an amorphous powder, which is contaminated with one equivalent of sodium bromide: IR (KBr) 1711, 1628, 1215 cm$^{-1}$; $^1$H NMR (DMSO-d$_6$, 300 MHz) δ 3.70 (s, 3H), 3.77 (s, 2H), 7.33–7.41 (m, 3H), 7.48 (s, 1H), 7.87–7.89 (m, 2H); $^{13}$C NMR (75 MHz, DMSO-d$_6$) δ 49.88, 51.93, 127.36, 128.33, 128.91, 129.82, 134.75, 139.06, 168.60.

Example 1D

2-Carbomethoxy-3-phenylpropane-1-sulfonic Acid Sodium Salt

To the 8 L of 1:1 methanol/water mixture containing the resultant compound from Example 1C was added 60 g of W-24 raney nickel. The resulting suspension was pressurized under 50 psi of hydrogen and was allowed to shake on a Parr shaker for 24 hours, at which time an additional 20 g of raney nickel catalyst was added. After 6 hours under 50 psi of hydrogen, the catalyst was removed by filtration and the solution was concentrated to dryness. To the dry white solid, ethyl acetate (6 L) and heptane (4 L) were added and the solution was vigorously stirred with a mechanical stirrer overnight. The white suspended solid was removed by filtration yielding 530 g (88%) of the desired product as an amorphous powder that was contaminated with approximately one equivalent of sodium bromide. The compound was used without any additional purification: IR (KBr) 1740, 1215, 1050 cm$^{-1}$. $^1$H NMR (DMSO-d$_6$, 300 MHz) δ 2.48–2.54 (m, 1H), 2.74–2.87 (m, 2H), 2.91–3.04 (m, 2H), 3.48 (s, 3H), 7.12–7.32 (m, 5H); $^{13}$C NMR (75 MHz, D$_2$O/DMSO-d$_6$) δ 38.18, 44.80, 52.67, 52.82, 127.42, 129.13, 129.34, 138.14, 176.84.

Example 1E

2-Carbomethoxy-3-phenyl-1-propanesulfonyl Chloride

To a 3 L round bottom flask was added the resultant compound from Example 1D (530 g, 1.39 mol) and toluene (520 mL) followed by the addition of phosphorous pentachloride (317 g, 1.52 mol). The mixture was warmed to 50° C. with stirring for 45 minutes. It was then diluted with toluene (1 L) and filtered through celite. After concentration in vacuo, 371 g (96%) of the desired product was obtained as a light brown oil: IR (film); 1740, 1380, 1170 cm$^{-1}$; $^1$H NMR (CDCl$_3$, 300 MHz) δ 2.92 (dd, 1H, J=8.1, 14.0), 3.17 (dd, 1H, J=6.6, 14.0), 3.41–3.50 (m, 1H), 3.67 (dd, 1H, J=3.3, 14.3), 3.72 (s, 3H), 4.20 (dd, 1H, J=8.8, 14.3), 7.15–7.18 (m, 2H), 7.25–7.35 (m, 3H); $^{13}$C NMR (75 MHz, CDCl$_3$) δ 37.26, 42.88, 52.65, 64.89, 127.49, 128.87, 128.92, 135.61, 171.79.

Example 1F

Methyl 2-Benzyl-3-(1-methyl-piperazin-4-ylsulfonyl )propionate

To a 1 L round bottom flask was added the resultant compound from Example 1E (84.5 g, 0.305 mol) and dichloromethane (305 mL). The mixture was cooled to 0° C. in an ice water bath and a solution of N-methyl piperazine (35.5 mL, 32.1 g) dissolved in dichloromethane (305 mL) was added dropwise with vigorous stirring over 90 minutes. After the addition was completed, the ice-water bath was removed and the mixture was stirred an additional 4 hours while warming to ambient temperature. The solution was then poured into a separatory funnel containing 1 L of a 5% aqueous sodium hydroxide solution. The layers were partitioned and the organic layer was dried over potassium carbonate. Concentration in vacuo yielded an oil, which was filtered through 200 g of silica gel using 4:1 hexane/ethyl acetate as an eluant. Concentration gave 84.3 g (81%) of the desired product as a yellow oil: IR (film); 1735, 1165, 955 cm$^{-1}$; $^1$H NMR (CDCl$_3$, 300 MHz) δ 2.30 (s, 3H), 2.42 (t, 4H, J=4.8), 2.88 (dd, 1H, J=7.7, 14.0), 2.93 (dd, 1H, J=3.7, 14.0), 3.06 (dd, 1H, J=7.0, 13.6), 3.18–3.27 (m, 5H), 3.43 (dd, 1H, J=8.82, 13.9), 3.67 (s, 3H), 7.14–7.17 (m, 2H), 7.24–7.34 (m, 3H); $^{13}$C NMR (75 MHz, CDCl$_3$) δ 37.91, 42.22, 45.36, 45.83, 49.61, 52.21, 54.36, 127.06, 128.66, 128.92, 129.06, 136.79, 173.33.

Example 1G (2S) 2-Benzyl-3-(1-methyl-piperazin-4-ylsulfonyl)propionic Acid

The resultant racemic ester from Example 1F (135 g, 397 mmol) was suspended in acetone (300 mL) and water (900 mL). To the vigorously stirred suspension at 25° C. was added a crude preparation of Subtilisin Carlsberg (10 mL, Alcalase 2.4L, Novo Laboratories). Sodium hydroxide solution (6M) was used to maintain the reaction at pH 7.5–8.0. After 3 days, the acetone was removed under reduced pressure and the aqueous phase was extracted with chloroform (1 L) to remove the unreacted ester. The aqueous phase was adjusted to pH 7 with 3M HCl and was desalted by eluting through a column of Amberlite XAD-16(2 kg, prewashed sequentially with water, methanol, and water) using a water to water/methanol gradient. Evaporation of the solvent afforded 46 g (70%) of a white solid: m.p. 184.5° C.; TLC (25% ethyl acetate/25% water/25% acetic acid/25% n-butanol) R$_f$=0.43; Anal.cacld for C$_{15}$H$_{22}$N$_2$O$_4$S.0.25 H$_2$O: C, 54.44; H, 6.85; N, 8.47. Found: C, 54.77; H, 6.53; N, 8.39.

Example 1H

Diethyl (2-bromoallyl)acetamidomalonate

To a stirred mixture of diethyl acetamidomalonate (217 g, 1.0 mol) and 2,3-dibromopropene (240 g, 1.2 mol) in anhydrous tetrahydrofuran (2.50 L), under nitrogen, was added sodium hydride (26.4 g, 1.1 mol) in several portions. The reaction mixture was stirred at ambient temperature for 30 minutes, then heated to reflux. After heating for 18 hours, the resultant slurry was cooled to ambient temperature and suction filtered through a short pad of silica gel. The solid residue was washed with tetrahydrofuran (2×50 mL), and the filtrates were combined and concentrated. The residue obtained was dissolved in ethyl acetate (2.0 L), washed with water and brine, and then was dried over magnesium sulfate. Filtration and concentration gave a yellow oil which solidified upon drying. The resultant solid was recrystallized from a mixture of hot ethyl acetate/hexane to give 301 g (89%) of the desired product: m.p. 85°–87° C. $^1$H NMR (300 MHz, CDCl$_3$) δ 1.28 (t, J=7.4 Hz, 6H), 2.04 (s, 3H), 3.57 (s, 2H), 4.27 (m, 4H), 5.55 (bs, 1H), 5.61 (bs, 1H) , 6.82 (broad, 1H); IR (KBr) 1745, 1635 cm$^{-1}$. Anal calcd for C$_{12}$H$_{18}$BrNO$_5$: C, 42.87; H, 5.40; Br, 23.77; N, 4.12. Found: C, 43.25; H, 5.56; Br, 22.97; N, 4.12.

Example 1I

Diethyl (3-bromo-2-oxo-propyl)acetamidomalonate

To a cold (0° C.), stirred solution of the resultant compound from Example 1H (280 g, 0.83 mol) in a mixture of 2: 1 acetonitrile/water (1.68 L) was added solid N-bromosuccinimide (193 g, 1.08 mol) in three portions over a period of 15 minutes. The resultant orange mixture was stirred at 0° C. for an additional period of 1 hour and then was allowed to warm to ambient temperature. After 4 hours, the reaction mixture was treated with 10% aqueous sodium thiosulfate, diluted with ethyl acetate, and washed sequentially with water, 10% aqueous sodium hydrogen sulfate (3×), water, and brine. Drying over magnesium sulfate and concentration afforded a yellow solid which was recrystallized from a mixture of ethyl acetate and hexane to give 247 g (85%) of the desired compound as a white solid: m.p. 97°–98.5° C. $^1$H NMR (300 MHz, CDCl$_3$) δ 1.25 (t, J=7.5 Hz, 6H), 2.01 (s, 3H), 3.87 (s, 2H), 3.93 (s, 2H), 4.25 (q, J=7.5 Hz, 4H), 7.0 (broad, 1H); IR (KBr) 1760, 1732, 1634 and 1209 cm$^{-1}$. Anal calcd for C$_{12}$H$_{18}$BrNO$_6$: C, 40.93; H, 5.15; Br, 22.62; N, 3.98. Found: C, 41.05; H, 5.23; Br, 23.28; N, 3.93.

Example 1J

Diethyl (4-thiazolylmethyl)acetamidomalonate

A 5 L, 3-neck round bottom flask equipped with a mechanical stirrer, stopper and a drying tube was charged with the resultant compound from Example 1I (325 g, 0.92 mol) and flushed with nitrogen. A freshly prepared solution of thioformamide in tetrahydrofuran (0.8M, 1.25 L) was added in one portion. The reaction mixture was stirred at ambient temperature for 4 hours. The resultant slurry was then diluted with ether (1.25 L) and cooled to 0° C. The solid was then collected by suction filtration and washed with cold ether (3×) to give the title compound as its hydrobromide salt. This material was transferred to a 4 L separatory funnel, slurried with ethyl acetate (2 L) and basified by the careful addition of 2M aqueous sodium hydroxide. The organic layer was separated, washed with water and brine, and then dried over magnesium sulfate. Filtration and concentration afforded a pale yellow oil which solidified upon drying to give 242 g of the desired compound. This material was recrystallized from ethyl acetate/hexane to afford 185.6 g (64%) of pure material: m.p. 104°–106° C. Anal calcd for C$_{13}$H$_{18}$N$_2$O$_5$S: C, 49.67; H, 5.77; N, 8.91; S, 10.20. Found: C, 49.90; H, 5.72; N, 8.97; S, 10.29.

Example 1K

N-Acetyl-3-(4-thiazolyl)-DL-alanine Ethyl Ester

To a stirred solution of the resultant compound from Example 1J (185.6 g, 0.59 mol) in a mixture of tetrahydrofuran (620 mL) and ethanol (310 mL) was added aqueous 2M lithium hydroxide (325 mL, 0.65 mol) dropwise over 20 minutes. After stirring at ambient temperature for 2.5 hours, the reaction mixture was concentrated. The resultant aqueous mixture was washed with ether (3×200 mL), adjusted to pH 3 with 3M hydrochloric acid, and concentrated under reduced pressure. Residual water was removed by chasing the residue with toluene (2×200 mL). The residue was then diluted with toluene (1.5 L) and the resultant slurry was heated to reflux with separation of residual water (Dean-Stark trap). After 3 hours the reaction mixture was cooled to ambient temperature, diluted with ethyl acetate (1.5 L) and suction filtered through silica gel (60 g). The removed solids were washed with additional ethyl acetate (4×500 mL) and the combined organic solutions were concentrated to afford a pale yellow oil which solidified on drying (0.5 torr) to afford 119.6 g (84%) of the desired compound: m.p. 58°–62° C.

Example 1L

N-Acetyl-3-(4-thiazolyl)-L-alanine and
N-Acetyl-3-(4-thiazolyl)-D-alanine Ethyl Ester A 5 L, 3-neck round bottom flask equipped with a mechanical stirrer was charged with the resultant compound from Example 1K (210 g, 0.87 mol), distilled water (1.6 L), and 1M aqueous potassium chloride (0.8 L). The homogeneous solution was adjusted to pH 7.0 with 0.1M sodium hydroxide and then treated with Subtilisin Carlsberg (1.8 g) dissolved in 0.1M aqueous potassium chloride (25 mL). The reaction mixture was stirred at ambient temperature with 1.0M sodium hydroxide added as required to maintain the pH at 6.25–7.25. After 4 hours, 430 mL of sodium hydroxide had been consumed and the reaction was judged to be complete. The reaction mixture was then extracted with chloroform (4×1.5 L), the aqueous phase was carefully acidified to pH 4 with 2M hydrochloric acid and then was concentrated under reduced pressure. Residual water was removed by consecutive chasing with toluene (3×500 mL) and ethanol (3×500 mL). The residue was taken up in warm ethanol and suction filtered to remove inorganic salts. The solids were washed with warm ethanol (3×400 mL) and the filtrate was concentrated to afford 92.6 g (50%) of N-acetyl-3-(4-thiazolyl)-L-alanine as a white solid: m.p. 186° C.

The combined chloroform fractions from the extractions were washed with saturated aqueous sodium bicarbonate, water, and brine and then were dried over magnesium sulfate. Filtration and concentration gave 103 g (49%) of N-acetyl-3-(4-thiazolyl)-D-alanine ethyl ester. This material could be further purified by recrystallization from ethyl acetate/hexane: m.p. 79°–80.5° C.

Example 1M

Epimerization of N-Acetyl-3-(4-thiazolyl)-D-alanine Ethyl Ester

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 1L (102 g, 0.42 mol) was added. The reaction mixture was then heated to reflux. After 3 hours the solution was cooled to ambient temperature, quenched with glacial acetic acid (0.045 mol) and concentrated to remove ethanol. The residue was diluted with ethyl acetate, washed with water and brine and dried over magnesium sulfate. Filtration and concentration gave a yellow oil which was purified by recrystallizing from a mixture of hot ethyl acetate and hexane to yield 89 g (87%) of material identical to that obtained from Example 1K.

Example 1N 3-(4-Thiazolyl)-L-alanine Dihydrochloride

A 2 L round bottom flask equipped with a magnetic stirrer was charged with N-acetyl-3-(4-thialzoyl)-L-alanine from Example 1L (92.6 g, 0.43 mol) and 6M hydrochloric acid (1 L). The resultant solution was heated to reflux. After 3 hours the mixture was allowed to cool to ambient temperature. The solution was then concentrated under reduced pressure, evaporated from toluene (3×200 mL), and dried under vacuum overnight to give 120 g of a slightly wet solid. This material was used in the next reaction without further purification.

Example 1O

N-Boc-3-(4-thiazolyl)-L-alanine

A 4 L Erlenmeyer flask equipped with a mechanical stirrer was charged with the resultant compound from Example 1N ( 125.9 g) and tetrahydrofuran ( 1.5 L), and the mixture was adjusted to pH 6.6 with saturated aqueous sodium bicarbonate. The resultant solution was then adjusted to pH 8.9 with 3.0M sodium hydroxide and a solution of di-tert-butyldicarbonate (117.8 g, 0.51 mol) in tetrahydrofuran (150 mL) was added. The reaction mixture was vigorously stirred at ambient temperature for 40 hours. The tetrahydrofuran was removed under reduced pressure, the pH of the residue was adjusted to 2.0 with 3.0M hydrochloric acid and the mixture was extracted with ethyl acetate (3×300 mL). The combined extracts were dried over magnesium sulfate, filtered, and concentrated to give 150 g of a white solid. Recrystallization from hot 1:1 ethyl acetate/hexane (1.06 L) gave 107.6 g (82% from the resultant compound of Example 1L) of the desired compound: m.p. 115° C. $[\alpha]_D = +129.8$ (c=1.04, CHCl$_3$). Anal calcd for $C_{11}H_{16}N_2O_2$: C, 48.53; H, 5.88; N, 10.29. Found: C, 48.58; H, 5.91; N, 10.17.

Example 1P

2-Amino-1-cyclohexyl-3,4-dihydroxy-6-methylheptane (2S,3R, 4S)-2-[(tert-Butyloxycarbonyl)amino]-1-cyclohexyl-3,4-dihydroxy-6-methylheptane (5.05 g, 14.7 mmol, Luly et al., *J. Org. Chem.* 1988, 53, 6109) was stirred for 90 min in 4M hydrochloric acid in ethanol and then evaporated. Ether was added and evaporated 3 times and the residue was dried under high vacuum. The title compound was used without further purification.

Example 1Q

Boc-L-(4-Thiazolyl) Ala Amide of
(2S,3R,4S)-2-Amino-1-cyclohexyl-3,4-dihydroxy-6-methylheptane To the compound resulting from Example 1P was added 1-hydroxybenzotriazole (5.57 g, 41.2 mmol), the resultant acid from Example 1O (4.00 g, 14.7 mmol), dimethylformamide (60 mL) and N-methylmorpholine (3.40 mL, 30.9 mmol). The mixture was cooled to −23° C., treated with 1-(3-dimethylaminopropyl)-3-ethylcarbodiimide hydrochloride (4.03 g, 21.0 mmol). After 2 hours at −23° C. and 21 hours at ambient temperature, the mixture was poured into saturated sodium bicarbonate solution and extracted into ethyl acetate. The organic layer was washed with water and brine, then dried over sodium sulfate and evaporated to a white solid which was recrystallized from 1:15 (v/v) methylene chloride/ether (multiple crops) affording 6.28 g (86%) of the desired product as a flaky white solid: m.p. 159°–160° C.; TLC (15% CH$_3$OH/85% CHCl$_3$) R$_f$=0.63; $^1$H NMR (CDCl$_3$, 300 MHz) δ 0.88 (3H, d), 0.94 (3H, d),.1.46 (9H, s), 1.89 (1H, septet), 3.30–3.12 (3H, m), 3.37 (1H, dd), 4.10 (1H, m), 4.27 (1H, m) , 4.44 (1H, dd) , 6.18 (2H, br d) , 7.14 (1H, d) , 8.78 (1H, d) . Anal calcd for $C_{25}H_{43}N_3O_5S$: C, 60.33; H, 8.71; N, 8.44. Found: C, 60.43; H, 8.68; N, 8.51.

Example 1R

H-L-(4-Thiazolyl) Ala Amide of (2S,3R,4S)-2-Amino-1-cyclohexyl-3,4-dihydroxy-6-methylheptane Trifluoroacetic acid (50 mL) was slowly added via cannula to a solution of the resultant compound from Example 1Q ( 6.27 g, 12.6 mmol) in methylene chloride (50 mL) at 0° C. The reaction was stirred 3 hours at 0° C. and concentrated in vacuo (40° C. bath) to an oil which was basified to pH 10–11 with aqueous potassium carbonate. The product was extracted into chloroform, and the combined organic extracts were dried over sodium sulfate, filtered, and concentrated in vacuo to give a foam. Recrystallization from 1:4 (v/v) methylene chloride/hexane gave 5.00 g (100%) of the desired product as a fluffy white solid: m.p. 111°–112° C.; TLC (15% CH$_3$OH/85% CHCl$_3$) R$_f$=0.46; $^1$H NMR (CDCl$_3$, 300 MHz) δ 0.86 (3H, d), 0.95 (3H, d), 3.25–3.12 (3H, m), 3.33 (1H, dd), 3.80 (1H, dd), 4.25 (1H, m), 4.54 (1H, m), 7.13 (1H, d), 7.40 (1H, br d), 8.77 ( 1H, d) . Anal calcd for C$_{20}$H$_{35}$N$_3$O$_3$S: C, 60.42; H, 8.87; N, 10.57. Found: C, 60.05; H, 8.65; N, 10.42.

Example 1S

(2S)-2-Benzyl-3-(1-methylpiperazin-4-ylsulfonyl) propionyl-(L)-(4-Thiazolyl)Ala Amide of (2S,3R,4S)-2-Amino-1-cyclohexyl-3,4-dihydroxy-6-methylheptane To the resultant acid from Example 1G (1.000 g, 3.064 mmol), the resultant amine from Example 1R (1.110 g, 2.792 mmol), and 1-hydroxybenzotriazole (1.022 g, 7.563 mmol) in dimethylformamide (20 mL) was added N-methylmorpholine (0.35 mL, 3.2 mmol). The mixture was cooled to −23° C. and treated with 1-(3-dimethylaminopropyl )-3-ethylcarbodiimide hydrochloride (0.760 g, 3.96 mmol). After 2 hours at −23° C. and 14 hours at ambient temperature, the reaction was poured into saturated sodium bicarbonate solution (100 mL) and extracted into ethyl acetate (2×50 mL). The combined organic extracts were washed with water (2×50 mL) and brine (50 mL), dried over sodium sulfate and evaporated to afford 1.94 g of product. Recrystallization from ethanol (15 mL)/hexane (90 mL) afforded 1.559 (79%) of a white solid: m.p. 169°–170° C.; TLC (10% CH$_3$OH/90% CHCl$_3$) R$_f$=0.40; $^1$H NMR (CDCl$_3$, 300 MHz) δ 0.87 (3H, d), 0.95 (3H, d), 2.30 (3H, s), 4.63 (1H, dd), 6.23 (1H, d), 7.37–7.16 (6H, m), 7.43 (1H, d), 8.73 (1H, d) . Anal calcd for C$_{35}$H$_{55}$N$_5$O$_6$S$_2$.0.75 H$_2$O: C, 58.43; H, 7.91; N, 9.73. Found: C, 58.51; H, 7.74; N, 9.60.

EXAMPLE 2

Alternative Preparation of N-Boc-3-(4-thiazolyl)-L-alanine

Example 2A

Ethyl (2-Bromoallyl)acetamidoacetate

To a solution of the product of Example 1H (3.36 g, 10.0 mmol) in dimethylformamide (10 mL) was added sodium chloride (586 mg, 10.0 mmol), water (360 μL, 20 mmol) and 4N hydrochloric acid in dioxane (0.12 mL, 0.5 mmol). The reaction vessel was placed under a positive nitrogen pressure. The reaction mixture was heated at reflux for 24 hours and then concentrated in vacuo. The residue obtained was diluted with water (5 mL) and extracted with ether (3×15 mL). The combined organic extracts were decolorized with charcoal (0.5 g), dried over magnesium sulfate, filtered, and concentrated in vacuo to afford the title product (2.51 g, 95%) as a pale yellow oil. $^1$H NMR (300 MHz, CDCl$_3$) δ 1.29 (t, 3H), 2.04 (s, 3H), 2.99 (m, 2H), 4.22 (q, 2H), 4.79 (m, 1H), 5.53 (d, 1H), 5.68 (m, 1H), 6.44 (d, 1H); IR (film) 1195, 1220, 1370, 1540, 1660, 1740, 2990, 3050, and 3300 cm$^{-1}$. MS (DCI/NH$_3$) m/e 264/266 (M+H)$^+$, 281/283 (M+H+NH$_3$)$^+$. Anal calcd for C$_9$H$_{14}$NO$_3$Br: C, 40.92; H, 5.34; N, 5.30. Found: C, 42.04; N, 5.48; N, 5.26.

Example 2B

N-Boc-(2-Bromoallyl)glycine

A slurry of the product of Example 2A (16.2 g, 61.3 mmol) in 0.1N potassium chloride solution (300 mL) containing 0.2M pH 7.0 phosphate buffer (30 mL) was treated with a solution of Subtilisin Carlsberg (4 mg) in 0.1N potassium chloride solution (3 mL). The pH was maintained between 6.50 and 7.25 by addition of 2.0N sodium hydroxide solution via a pH-Stat. After 25 minutes, the rate of hydrolysis noticeably slowed; and the unreacted D-ester was extracted with methylene chloride (3×150 mL). The resulting aqueous phase was treated with cobalt(II) acetate (6 mg) and Acylase I (80 mg). The reaction mixture was stirred for 4 hours and determined to be complete.

The pH of the reaction mixture was adjusted to 10 by the addition of solid sodium carbonate. The resulting solution was treated with di-tert-butyl dicarbonate (6.55 g, 30 mmol) dissolved in tetrahydrofuran (100 mL) and vigorously stirred for 16 hours. The aqueous solution was washed with hexane (200 mL) to remove any unreacted protecting-reagent. The aqueous layer was adjusted to pH 2.5 by the addition of solid potassium hydrogen sulfate and extracted with ethyl acetate (2×200 mL). The combined organic layers were washed with brine (100 mL), dried over magnesium sulfate, and concentrated in vacuo to give the title compound (7.30 g, 81%) as a pale yellow crystalline solid. [α]$_D$ at 25° C.=−9.86° (MeOH), c=1.085. $^1$H NMR (300 MHz, CDCl$_3$) δ 1.48 (s, 9H), 2.91 (m, 2H), 4.52 (m, 1H), 5.19 (d, 0.5H), 5.53 (m, 1H), 5.71 (s, 1H), 6.79 (d, 0.5H), 11.3 (s, 1H); IR (CDCl$_3$) 1150, 1250, 1400, 1500, 1620, 1640, 1710, 3000, 3350, and 3520 cm$^{-1}$. (DCI/NH$_3$) m/e 311/313 (M+H+NH$_3$)$^+$. Anal calcd for C$_{10}$H$_{16}$NO$_4$Br: C, 42.12; H, 5.66; N, 4.91. Found: C, 41.38; H, 5.59; N, 4.75.

Example 2C

(2R)-N-Boc-2-Amino-5-bromo-4-oxopentanoic Acid

To a solution of the product of Example 2B (2.00 g, 6.80 mmol) in water (30 mL) and tetrahydrofuran (15 mL) cooled to 0° C. was added N-bromosuccinimide (1.45 g, 8.16 mmol) in three portions over twenty minutes. After the addition was complete, the ice bath was removed and the solution was stirred for four hours. The tetrahydrofuran was removed in vacuo and the product was extracted with ethyl acetate (3×35 mL). The organic extracts were combined and washed with 5% sodium chloride solution (25 mL) and brine (25 mL), dried over magnesium sulfate, and concentrated in vacuo to afford the title compound (1.70 g, 81%). $^1$H NMR (300 MHz, CDCl$_3$) δ 1.45 (s, 9H), 3.30 (m, 2H), 3.93 (s, 2H), 4.61 (m, 1H), 5.51 (d, 1H). MS (DCI/NH$_3$) m/e 310/312 (M+H)$^+$, 327/329 (M+H+NH$_3$)$^+$.

Example 2D

(2R)-N-Boc-2-Amino-3-(4-thiazolyl) propanoic Acid

To a solution of the product of Example 2C (91 mg, 0.293 mmol) in tetrahydrofuran (5 mL) was added thioformamide (17.7 mg, 0.29 mmol). [Thioformamide was prepared by reacting a slight excess of phosphorus pentasulfide with formamide in tetrahydrofuran. The resulting solution was diluted with hexanes and filtered through a silica gel plug and stored at −25° C.] The resulting solution was allowed to stand for sixteen hours and then concentrated in vacuo to afford a residue which was partitioned between diethyl ether and aqueous sodium bicarbonate. The aqueous layer was washed with ether (2×10 mL) and methylene chloride (10 mL), adjusted to pH 2.3 with solid potassium hydrogen sulfate, and extracted with ether (3×20 mL). The combined organic extracts were dried over magnesium sulfate and concentrated in vacuo to afford the title compound as a white crystalline solid (55 mg, 71%). $^1$H NMR (300 MHz, CDCl$_3$) δ 1.48 (s, 9H), 3.48 (m, 2H), 4.52 (m, 1H), 5.61 (m, 1H), 7.18 (d, 1H), 8.91 (d, 1H).

EXAMPLE 3

Alternative Preparation of N-Acetyl-3-(4-thiazolyl)-DL-alanine Ethyl Ester

Example 3A

N-Acetyl-2-(3-Bromo-2-oxopropyl)-glycine ethyl ester

To a solution of diethylacetamidomalonate (65.16 g, 300 mmol) in 300 mL of anhydrous DMF was added 97% sodium t-butoxide (31.21 g, 315 mmol). The resulting solution was allowed to exotherm to ca. 45° C. and stirred 1 hour. To the resulting enolate was added 2,3-dichloropropene (The 2,3-dichloropropene was distilled prior to use to remove some trace colored impurities and remove any hydrogen chloride, alternatively one could pass the 2,3-dichloropropene through basic alumina, or use as is from vendor.) (30.42 mL, 330 mmol). The solution was then heated to ca. 100° C. for 4 hours, cooled to ambient temperature and treated with 30 mmol hydrochloric acid in 11.88 mL of water (660 mmol). The solution was then treated with lithium bromide (26.1 g, 300 mmol) to afford a thick slurry. The reaction mixture was then heated at strong reflux for 6 hours, cooled to ambient temperature and concentrated in vacuo at 80° C. The residue was dissolved in ethanol (250 mL) and water (500 mL) and treated with sodium bicarbonate (30.24 g, 360 mmol. The resulting solution was cooled to 0° C. and treated with bromine (17.0 mL, 330 mmol) in portions over 45 minutes. The resulting suspension was stirred at 0° C. for an additional 2 hours and allowed to warm to ambient temperature and stirred overnight. The solution was extracted with 4×500 mL of methylene chloride. The combined organic extracts were washed with 200 mL of a 1:1 solution of saturated sodium chloride and sodium carbonate, dried over magnesium sulfate, filtered and concentrated in vacuo to afford 69 g of a dark tan solid. A portion of this solid (43 g) was slurried in 250 mL of a hot 2:1 solution of hexanes and ethyl acetate and stirred for 30 minutes at 45°–50° C. The slurry was then cooled to 0° C. with stirring for 30 minutes, filtered and the solid washed with 2:1 hexanes/ethyl acetate (3×20 mL). The product was dried to a constant weight of 31.0 g (59%). m.p. 120.9° C. $^1$H NMR (CDCl$_3$, 300 MHz) δ 1.38 (t, 3H), 2.03 (s, 3H), 3.32 (dq, 2H), 3.89 (d, 2H), 4.21 (q, 2H), 4.71 (m, 1H), 6.42 (bd, 1H).

Example 3B

N-Acetyl-2-bromothiazoylalanine Ethyl Ester

To a slurry of the compound resulting from Example 3A (14.0 g, 50 mmol) in 30 mL of glacial acetic acid was added potassium thiocyanate (4.85 g, 51 mmol). The resulting suspension was stirred vigorously using an overhead stirrer and allowed to exotherm to ca. 30° C. After 15 minutes the slurry became a thick crystalline mass, which was stirred for an additional 2 hours. The mass was treated with 50 mL of 30% hydrobromic acid in acetic acid. The reaction was judged complete at 1 hour, and the resulting solution was allowed to stand overnight at ambient temperature. The slurry was then poured into 300 mL of diethyl ether and stirred for 20 minutes. The product and co-precipitated potassium bromide were removed by filtration and dried to a constant weight of 28.0 g.

Example 3C

N-Acetyl-3-(4-thiazolyl)-DL-alanine Ethyl Ester

A solution of 1.43 mL of glacial acetic acid, sodium acetate (1.025 g, 12.5 mmol) in 40 mL of water was treated with the product resulting from Example 3B. The resulting slurry was treated with zinc dust (2.48 g, 38 mmol) and the resulting solution was stirred for 30 minutes. Ethyl acetate (50 mL) was added, and the suspension was filtered to remove unreacted zinc dust. The filter cake was washed with 3×15 mL of ethyl acetate. The organic layer was separated from the aqueous layer and the aqueous layer was extracted with 2×25 ml of methylene chloride. The combined organic extracts, including the ethyl acetate solution, were washed with saturated potassium carbonate and 20 mL of brine, dried over magnesium sulfate, filtered and concentrated in vacuo to afford 2.55 g of pure d,1-N-acetylthiazoylalanine ethyl ester. The combined yield for steps 3B and 3C was 85%. $^1$H NMR (CDCl$_3$, 300 MHz) δ 1.22 (t, 3H), 2.03 (s, 3H), 3.32 (dq, 2H), 4.23 (q, 2H), 4.92 (m, 1H), 6.79 (bd, 1H), 8.78 (d, 1H).

EXAMPLE 4

Alternative Preparation of N-Acetyl-3-(4-thiazolyl)-DL-alanine Ethyl Ester Hydrobromide A solution of the compound resulting from Example 3A (5.65 g, 20.16 mmol) and thioformamide (1.23 g, 20.16 mmol) in acetone (50 mL) was refluxed for 2 hours and then allowed to stir for 48 hours at ambient temperature. The title compound precipitated from solution as the hydrobromide salt which was removed from solution by filtration and washed with 2×15 mL of acetone. The solid was dried to a constant weight of 5.15 g (80%).

EXAMPLE 5

Alternative Preparation of (2R)-N-Boc-2-Amino-5-bromo-4-oxopentanoic acid

Example 5A

Diethyl (2-Chloroallyl) acetamidomalonate

To a suspension of 95% sodium hydride (17.2 g, 680 mmol) in tetrahydrofuran (1.2 L) was added 2,3- dichloropropene (100 g, 900 mmol), diethylacetamidomalonate (146 g, 672 mmol) and tetrabutylammonium bromide (6.00 g) . The resulting thick suspension was warmed at reflux under nitrogen for 20 hours. The reaction mixture was concentrated in vacuo and the resulting residue was partitioned between water (200 mL) and a mixture of ether (300 mL) and methylene chloride (100 mL). The organic phase was washed with 5% sodium chloride solution (200 mL) and brine (200 mL), dried over magnesium sulfate, filtered, and concentrated in vacuo. The resulting solid (195 g) was dissolved in hot hexanes (1300 mL) and allowed to cool to ambient temperature and sit overnight to afford the title compound as a crystalline solid (157 g, 80%). m.p. 76.3° C. $^1$H NMR (300 MHz, CDCl$_3$) $\delta$ 1.29 (t, 6H), 2.05 (s, 3H), 3.48 (s, 2H), 4.28 (m, 4H), 5.18 (m, 1H), 5.29 (m, 1H), 6.92 (bs, 1H); IR (CDCl$_3$) 1140, 1180, 1200, 1240, 1270, 1300, 1500, 1630, 1680, 1740, 2950, 2990, and 3300 cm$^{-1}$. MS (DCI/NH$_3$) m/e 292/294 (M+H)$^+$, 309/311 (M+H+NH$_3$)$^+$. Anal calcd for C$_{12}$H$_{18}$NO$_5$Cl: C, 49.41; H, 6.22; N, 4.80. Found: C, 49.18; H, 6.29; N, 4.75.

Example 5B

Ethyl (2-Chloroallyl)acetamidoacetate

The product of Example 5A (137 g, 500 mmol) was hydrolyzed and decarboxylated by the procedure described in Example 2A to afford the title compound (105.4 g, 96%) as a pale yellow oil which crystallized upon standing. $^1$H NMR (300 MHz, CDCl$_3$) $\delta$ 1.31 (t, 3H), 2.05 (s, 3H), 2.79 (m, 2H), 4.22 (q, 2H), 4.79 (m, 1H), 5.23 (m, 1H), 5.29 (m, 1H), 6.61 (m, 1H); IR 1200, 1220, 1280, 1300, 1370, 1440, 1550, 1638, 1659, 1740, 2890, 2990, 3050, and 3300 cm$^{-1}$. MS (DCI/NH$_3$) m/e 220/222 (M+H)$^+$, 237/239 (M+H+NH$_3$)$^+$. Anal calcd for C$_9$H$_{14}$NO$_3$Cl: C, 49 21; H, 6.42; N, 6.38. Found: C, 46.58; H, 6.05; N, 6.02.

Example 5C (2R)-N-Boc-2-Amino-5-bromo-4-oxopentanoic acid

The product of Example 5B is treated according to the procedure of Example 2B and 2C to provide the desired product .

EXAMPLE 6

Alternative Preparation of

2(S)

Benzyl-3-(1-methylpiperazin-4-ylsulfonyl)propionic acid

Example 6A

2-Carbomethoxy-3-phenylpropane-1-sulfonic acid Sodium salt

To a 0.3M ethanolic solution of the product of Example 1B, (Z)-1-bromo-2-carbomethoxy-3-phenyl-2-propene, (0.98 molar equivalents) was added over one hour at 50° C. a 1.4M aqueous solution of sodium sulfite (1.0 molar equivalent) . The mixture was stirred for 10 hours at 50° C., and then the ethanol was removed under reduced pressure at 50° C. Ethyl acetate (3 kg per 1 kg of bromide) was added and the mixture stirred for an additional 15 minutes and let stand for 10 minutes. The layers were separated and the aqueous layer was washed as above with two additional aliquots of ethyl acetate (1 kg per 1 kg of bromide).

Raney nickel (1 kg per 10 kg of aqueous solution) was added to the aqueous solution which was then evacuated and purged with nitrogen followed by hydrogen (3×) and placed under 40 psi of hydrogen for 6.5 to 9.5 hours. The Raney nickel was removed by filtration using nitrogen pressure, and the filtrate was concentrated under reduced pressure at 55° C. A 10% aqueous acetone solution (0.3 kg per 1 kg of starting bromide) was added to the residue obtained, and the mixture was warmed at 50° C. for 30 minutes. Additional acetone (3 kg per 1 kg of starting bromide) was slowly added over one hour to effect crystallization of the product. After stirring for one hour, the product was removed by filtration and washed with acetone to afford the title compound in 60–65%. m.p. 255° C. dec. A second crop was obtained by adding additional acetone (2.5 kg per 1 kg of starting bromide) and cooling to −20° C. for 10–12 hours and removing the second crop by filtration. An additonal 13–40% yield of title compound was obtained in that way.

Example 6B

Methyl 2-Benzyl-3-(1-methylpiperazin-4-ylsulfonyl)propionate

The product of Example 6A (1 molar equivalent) was mixed with phosphorus pentachloride (1.5 molar equivalents) and warmed at 70°–75° C. for 3–4 hours. The reaction mixture was cooled to ambient temperature and then diluted with toluene (16.7 molar equivalents) and added to 10% aqueous sodium chloride solution (4 kg per 1 kg of phosphorus pentachloride) while maintaining the temperature below 40° C. The mixture was stirred for 5 minutes, allowed to settle for 15 minutes, and then the phases were separated. The sodium chloride wash was repeated as described above. The toluene phase was cooled to 5° C. and N-methylpiperazine (3 molar equivalents in 3 molar equivalents of toluene) was added maintaining the temperature below 15° C. The mixture was stirred for 4–6 hours and then washed with 8% aqueous sodium hydroxide (2×3.4 kg per 1 kg of phosphorus pentachloride). The combined basic washes were re-extracted with toluene (0.25 kg per 1 kg of sodium hydroxide solution). The combined toluene extracts were washed with water (1 kg per 1 kg of phosphorus pentachloride), and the toluene was removed by distillation at reduced pressure to afford the title compound (65–70%) as a viscous oil which crystallizes on standing. MS (DCI/NH$_3$) m/e 341 (M+H)$^+$.

Example 6C (2S )-2-Benzyl-3- (1-methylpiperazin-4 -yl sulfonyl)propionic Acid

The product of Example 6B (69 kg, 20 mol) in acetone (420 kg)/water (960 kg) was adjusted to pH 8.0 using 1N sodium hydroxide. Alcalase TM (Novo Industries, Denmark) (Subtilisin Carlsberg) (6.9 liters) was added and the pH was maintained between 7.9 and 8.4 by the addition of 1N sodium hydroxide. When 80% of the theoretical amount of sodium hydroxide had been consumed, the reaction was quenched by the addition of ethyl acetate. The reaction mixture was concentrated to half the original volume under reduced pressure and then washed with ethyl acetate (2×700 kg). The volume of the aqueous phase was concentrated by half and the pH adjusted to 5.2. The reaction mixture was treated with XAD-16 resin (50 kg), stirred for 18 hours, and applied to an XAD-16 resin column (50 kg). The column was eluted with water (500 kg) and then 35% ethanol in water (1000 kg) to afford a residue which was treated with isopropanol (270 kg) and warmed to 75° C. Upon cooling to ambient temperature and subsequently to −5° C., crystalline material was obtained. The solid was removed by filtration, washed with cold isopropanol (30 kg) and dried at 50° C. to afford the title compound (13 kg, 49%). MS (DCI/NH$_3$) m/e 327 (M+H)$^+$. This compound can be recrystallized from 1:1 isopropanol/water.

EXAMPLE 7

Alternative Preparation of (2S,3R,4S) N-Boc-2-Amino-1-cyclohexyl-3,4-dihydroxy-6-methylheptane

Example 7A (4S,5R)-2,2-Dimethyl-4-(isobutyl-1-ene)-5-hydroxymethyl-1,3-dioxolane 2,3-O-Isopropylidene-D-erythrose was prepared by literature procedures (Cohen, N., et al.; J. Am. Chem. Soc. 105, 3661 (1983)) from D-isoascorbic acid. To a suspension of isopropyltriphenylphosphine (121 g, 2.4 equiv, 0.314 mol) in tetrahydrofuran (1.5 L) at −40° C. under nitrogen was added n-butyllithium (1.6M solution in hexanes) (197 mL, 2.4 equiv) dropwise. The erythrose (21 g, 1 equiv, 0.131 mol) in tetrahydrofuran (231 mL) was also added dropwise maintaining the temperature at −40° C. The mixture was then allowed to warm to ambient temperature and stirred under nitrogen for 20 hours and then quenched by the addition of ammonium chloride (77 g). The insoluble material was removed by filtration through Celite and the filtrate concentrated at reduced pressure to afford a residue which was extracted (4X) with ether. The combined ether extracts were washed with water and brine, dried over magnesium sulfate, and concentrated in vacuo to afford a yellow oil. Chromatography on silica gel eluting with 20% ethyl acetate in hexanes afforded the title compound (13.0 g, 53%). In a separate experiment, distillation gave the title compound in 42% yield, b.p. 59°–70° C. (0.25 mmHg). [α]$^{25}_D$+43.1° (c 1.65, CHCl$_3$) . IR (CDCl$_3$) 3680–3320 (OH) cm$^{-1}$. $^1$H NMR (DMSO-d$_6$, 300 MHz) δ 1.27 (s, 3H), 1.36 (s, 3H) , 1.63 (s, 3H), 1.69 (s, 3H) , 3.33 (t , J= 6 Hz, 2H), 4.06 (dd, J=6, 12 Hz, 1H), 4.57 (t, J=6 Hz, 1H), 4.81 (dd, J=9, 11 Hz, 1H), 5.64 (d, J=9 Hz, 1H). MS (DCI/NH$_3$) m/e 204 (M+H+NH$_3$)$^+$.

Example 7B (4S,5R)-2,2-Dimethyl-4-(isobutyl-1-ene)-5-formyl-1,3-dioxolane

To oxalyl chloride (1.66 mL, 1.1 equiv) in methylene chloride (29 mL) cooled to −60° C. was added dimethyl sulfoxide (2.01 mL, 2.2 equiv) in methylene chloride (5.5 mL). After 2 minutes, a solution of the product of Example 7A in methylene chloride (10 mL) was added. After stirring for 15 minutes at −60° C., triethylamine (8.23 mL, 5 equiv) was added. After stirring for an additional 5 minutes, the reaction mixture was allowed to warm to ambient temperature. Water was added and the phases were separated. The aqueous phase was extracted with chloroform (2X) and the combined organic extracts were washed with 1% hydrochloric acid and 5% sodium sulfite, dried over magnesium sulfate, and concentrated under reduced pressure to afford crude product. Chromatography on silica gel eluting with 10% ether in hexanes afforded the aldehyde (1.26 g, 57%). $^1$H NMR (CDCl$_3$, 300 MHz) δ 1.45 (s, 3H), 1.62 (s, 3H), 1.73 (s, 3H), 1.77 (s, 3H), 4.35 (m, 1H), 5.14 (m, 2H), 9.58 (d, J=6 Hz, 1H) .

Example 7C (4S,5R)-2,2-Dimethyl-4-(isobutyl-1-ene)-5-(formyl-N-benzylimine)-1,3-dioxolane To the compound resulting from Example 7B (1.26 g, 6.84 mmol) dissolved in toluene (32 mL) was added magnesium sulfate (1.64 g, 2 equiv); the reaction mixture was then cooled to 0°–5° C. Benzylamine (746 μL, 1 equiv) was added and the reaction mixture was stirred at 0°–5° C. for 90 minutes and then concentrated at reduced pressure. Methylene chloride was added, the insoluble material was removed by filtration, and the solvent was removed at reduced pressure to afford the title compound. $^1$H NMR (CDCl$_3$, 300 MHz) δ 1.42 (s, 3H), 1.57 (s, 3H), 1.63 (s, 3H), 1.68 (s, 3H), 4.53 (d, J=12 Hz, 1H), 4.62 (d, J=6 Hz, 1H), 470 (d, J=12 Hz, 1H), 5.05 (dd, J=9 Hz, 6 Hz, 1H), 5.15 (d, J=9 Hz, 1H), 7.20–7.37 (m, 5H), 7.64 (d, J=6 Hz, 1H).

Example 7D (4S,5R)-2,2-Dimethyl-4-(isobutyl-1-ene)-5-[(1S)-1-benzylamino-2-cyclohexyl)ethyl]-1,3-dioxolane Cerium(III) chloride heptahydrate (11 g, 5 equiv) was warmed at 150° C. under 0.15 mm of mercury vacuum for 2 hours with stirring. After cooling to ambient temperature, tetrahydrofuran (30 mL) was added. The mixture was stirred for 2 hours and then cooled to −40° C.

The Grignard reagent was prepared by the dropwise addition of cyclohexylmethyl bromide (4.12 mL, 30 mmol) dissolved in tetrahydrofuran (30 mL) to magnesium (717 mg, 30 mmol) and 1,2-dibromoethane (4–5 drops). After the reaction mixture had cooled to ambient temperature, it was cannulated into the cooled cerium(III) chloride solution and stirred for 30 minutes. The reaction mixture was allowed to warm to ambient temperature, stirred for 2 hours, and cooled to −40° C.

A solution of the imine resulting from Example 7C (1.62 g, 5.90 mmol, 1 equiv) in tetrahydrofuran was cannulated into the cooled reaction mixture. The reaction mixture was allowed to warm to ambient temperature and stirred overnight; ether was added followed by saturated sodium bicarbonate solution. The organic layer was separated, dried over magnesium sulfate, and concentrated under reduced pressure to afford crude compound (2.38 g, 100%). Chromatography on silica gel eluting with 20% ethyl acetate in hexane afforded the title product (368 mg, 17%). $^1$H NMR (CDCl$_3$, 300 MHz) δ 0.83–1.81 (m, 30H), 2.79 (t of d, J=3 Hz, 7.5 Hz, 1H), 3.45 (d, J=6 Hz, 2H), 3.86 (s, 1H), 4.08 (d of d, J=6 Hz, 9 Hz, 1H), 4.76 (d of d, J=10.5 Hz, 6 Hz, 1H), 5.26 (d, J=10.5 Hz, 1H) . MS (DCI/NH$_3$) m/e 372 (M+H)$^+$.

Example 7E (2S,3R,4S) N-Boc-2-Amino-1-cyclohexyl-3,4-dihydroxy-6-methylheptane The product of Example 7D (39 mg, 0.105 mmol) was dissolved in acidic methanol, treated with palladium on carbon, and placed under 4 atmospheres of hydrogen. The catalyst was removed by filtration through Celite and the filtrate concentrated at reduced pressure to afford the amine salt (29 mg, 100%). The 300 MHz $^1$H NMR spectrum was found to be consistent with the proposed structure. MS (DCI/NH$_3$) m/e 228 (M+H)$^+$, 244 (M+H+NH$_3$)$^+$.

To the amine salt (14.1 rag, 0.058 mmol) dissolved in methylene chloride (1 mL) was added N-methylmorpholine (NMM) (164 μL, 2.5 equiv) followed by di-tert-butyl dicarbonate (15 mg, 1.2 equiv). The reaction mixture was stirred overnight and then washed with saturated sodium bicarbonate, dried over magnesium sulfate, and concentrated under reduced pressure to afford the title compound (15.3 mg, 77%). $^1$H NMR (CDCl$_3$, 300 MHz) δ 0.89 (d, J=7 Hz, 3H), 0.95 (d, J=7 Hz, 3H), 1.10– 1.81 (m, 15H), 1.45 (s, 9H), 1.94 (m, 1H), 3.20 (d, J=8 Hz, 1H), 3.34 (m, 1H), 4.04 (br m, 2H), 4.25 (bd, 1H), 4.55 (bd, 1H).

EXAMPLE 8

Alternative Preparation (2S,3R,4S) N-Boc-2-Amino-1-cyclohexyl-3,4-dihydroxy-6-methylheptane

Example 8A (4S,5R)-2,2-Dimethyl-4-(2-methylpropan-1-yl)-5-hydroxymethyl-1,3-dioxolane A solution of the alcohol resulting from Example 7A (7.56 g) dissolved in 150 mL of methanol was added 529 mg of 10% Pd on carbon (dry). The mixture was placed under 1 atmosphere of hydrogen at ambient temperature for 24 hours. The catalyst was removed by filtration and washed with methanol. The combined methanol filtrates were evaporated in vacuo to give a thick oil (7.31 g, 96%). b.p. 81° C. (0.7 mm Hg). [α]$^{25}_D$= +26.3° (c 2.2, CHCl$_3$); IR (CDCl$_3$) 3680–3320 (OH) cm$^{-1}$; $^1$H NMR (CDCl$_3$, 300 MHz) δ 0.93 (d, J=9 Hz, 3H), 0.96 (d, J=9 Hz, 3H), 1.28-1.18 (m, 1H), 1.85 (dd, J=4, 6 Hz, 1H),4.26 (m, 1H), 1.37 (s, 3H), 1.47 (s, 3H), 1.59-1.48 (m, 1H), 1.82-1.69 (m, 1H), 3.60 (m, 2H), 4.12 (dd, J=6 Hz, 1H). MS (DCI/NH$_3$) m/e 189 (M+H)$^+$, 206 (M+H+NH$_3$)$^+$.

Example 8B (4S,5R)-2,2-Dimethyl-4-(2-methylpropan-1-yl)-5-formyl-1,3-dioxolane N,N-Dimethylhydrazone Oxalyl chloride (0.51 mL, 5.8 mmol) in 14 mL methylene chloride was cooled to −60° C. in a dry ice/chloroform bath. Dimethyl sulfoxide (0.9 mL, 11.7 mmol) in 1.0 mL methylene chloride was added and the reaction mixture was stirred for 3 minutes. The alcohol resulting from Example 8A (1.0 g, 5.31 mmol) in 2.0 mL of methylene chloride was added in one portion maintaining the temperature at −40° C. After 15 minutes, triethylamine (3.7 mL, 26.6 mmol) was added dropwise and the mixture was stirred for 5 minutes, warmed to ambient temperature, and N,N-dimethylhydrazine (1.61 mL, 1.28 g, 21.2 mmol) and magnesium sulfate (1.3 g) were added. The mixture was stirred for 1 hour at ambient temperature. Water (100 mL) was added and the organic layer was separated, washed with saturated aqueous sodium chloride, dried over magnesium sulfate, and filtered. Evaporation of the filtrate gave the hydrazone as a yellow oil. The crude hydrazone was purified by silica gel chromatography using (7:93) ethyl acetate:hexane to afford 808 mg (62%) of the title compound as a colorless oil. $^1$H NMR (CDCl$_3$, 300 MHz) δ 0.90 (d, J=6 Hz, 3H), 0.95 (d, J=6 Hz, 3H), 1.29-1.19 (m, 1H), 1.38 (s, 3H), 1.53-1.42 (m, s, 4H), 1.85-1.67 (bm, 1H), 2.82 (s, 6H), 4.33-4.25 (m, 1H), 4.6 (dd, J=7,8 Hz, 1H), 6.41 (d, J=6 Hz, 1H). MS (DCI/NH$_3$) m/e 229 (M+H)$^+$.

Example 8C (4S,5R)-2,2-Dimethyl-4-(2-methylpropan-1-yl)-5-[(1S)-1-N,N-dimethylhydrazino-2-cyclohexyl)ethyl]-1,3-dioxolane Using the procedure described in Example 8B and the following amounts of these reagents: oxalyl chloride (5.1 mL, 58 mmol), 140 mL methylene chloride, DMSO (9.1 mL, 117 mmol), the compound resulting from Example 8A (10 g, 53.1 mmol), triethylamine (37 mL, 266 mmol), N,N-dimethylhydrazine (16.1 mL, 12.8 g, 212 mmol), and magnesium sulfate (12.7 g) gave the crude hydrazone which was used in the next step without further purification.

To a solution of t-BuLi (1.7M in pentane, 91 mL, 154 mmol) cooled to −80° to −90° C. using a diethyl ether/liquid nitrogen bath was added 17.9 g (80 mmol) of cyclohexylmethyl iodide, which was prepared according to the procedure of Kropp et al.; J. Org. Chem. 48, 2084–90 (1983). After 5 minutes, the temperature of the reaction mixture was allowed to rise to −10° C. and a solution of the crude hydrazone in 60 mL of ether was added. After the addition, the mixture was allowed to warm to ambient temperature over 1 hour, re-cooled in an ice-water bath, and water was added. The aqueous layer was separated and the ether layer washed with aqueous saturated sodium chloride, dried over magnesium sulfate, filtered, and evaporated to give the hydrazine as a yellow oil (11.55 g, 66% crude recovery) which was used without further purification. $^1$H NMR (CDCl$_3$, 300 MHz) δ 0.92 (d, J=6 Hz, 3H), 0.97 (d, J=6 Hz, 3H), 1.3 (s, 3H), 1.44 (s, 3H), 1.86 (m, 2H), 2.44 (s, 6H), 2.85 (td, J=3, 9 Hz, 1H), 4.07 (m, 2H). MS (FAB) m/e 327 (M+H)$^+$.

Example 8D (2S,3R,4S) N-Boc-2-Amino-1-cyclohexyl-3,4-dihydroxy-6-methylheptane To the crude hydrazine dissolved in 250 mL of methanol was added 27 g of 2800 Raney nickel. The mixture was placed under 4 atmospheres of hydrogen at ambient temperature for 48 hours. The catalyst was removed by filtration through a 45 micron filter and washed with water (3×) and methanol (3×). The methanol was removed under reduced pressure to give 9.37 g of the amine as a green oil (80% recovery). $^1$H NMR (CDCl$_3$, 300 MHz) δ 0.92 (d, 3H, J=6 Hz), 0.98 (d, 3H, J=6 Hz), 1.85 (m, 2H), 2.93 (m, 1H), 3.76 (t, 1H, J=6 Hz), 4.15 (ddd, 1H, J=3,6,12 Hz). MS (FAB) m/e 284 (M+H)$^+$.

The crude amine was dissolved in 220 mL methanol and 27.5 mL 6N HCl, stirred at ambient temperature for 4 hours and evaporated at 0.25 mm Hg to give a brown amorphous solid. To this crude amine hydrochloride dissolved in 100 mL of THF were added N-methyl morpholine (7.21 mL, 65.6 mmol) and di-tert-butyl dicarbonate (10.7 g, 49.2 mmol). After 2 hours at ambient temperature, the solution was evaporated under reduced pressure. The residue obtained was dissolved in ethyl acetate, washed with saturated aqueous sodium bicarbonate, filtered, evaporated under reduced pressure, and the residue obtained redissolved in hexane.

The title product crystallized on standing at ambient temperature (3.9 g, 24% from Example 8A). TLC analysis using (2:98) methanol:methylene chloride showed one compound, $R_f=0.32$. An analytical sample was obtained by recrystallization from hot (2:7) ethyl acetate:hexane to give a white solid. m.p. 124°–127° C. (Lit. 124°–126° C.); $[\alpha]^{25}_D = -63.6°$ (c 2.20, CHCl$_3$) [Lit. $-64.91°$ (c 2.20, CHCl$_3$)]. $^1$H NMR (CDCl$_3$, 300 MHz) δ 0.88 (d, J=6 Hz, 3H), 0.94 (d, J=6 Hz, 3H), 1.47 (s, 9H), 1.93 (m, 1H), 3.2 (t, J=6 Hz, 1H), 3.33 (m, 1H), 4.05 (m, 1H), 4.56 (d, J=9 Hz, 1H). MS (FAB) m/e 344 (M+H)$^+$. Anal calcd for C$_{19}$H$_{37}$NO$_3$: C, 66.43; H, 10.86; N, 4.08. Found: C, 66.93; H, 10.91; N, 4.10.

EXAMPLE 9

Alternative Preparation of (4S,5R)-2,2-Dimethyl-4-isobutyl-5-formyl-1,3-dioxolane

Example 9A (4S,5R)-2-Methyl-4,5-dihydroxy-hept-2-ene

Cuprous iodide (152 mg, 0.08 mmol) was added to 40 mL of THF (distilled over Na benzophenone ketyl) and cooled to −40° C. while stirring under a nitrogen atmosphere. Isopropylmagnesium chloride (2.0M in diethyl ether, 17.1 mmol, 8.5 mL) was added by syringe, followed by an injection of (2S,3R)-1,1-epoxypent-4-en-3-ol, (Schreiber, S. L.; Schreiber, T. S.,; Smith, D. B.; J. Amer. Chem. Soc. 109, 1525 (1987)), (1 g, 9.98 mmol) dissolved in 20 mL THF. The resulting mixture was stirred at −40° C. for 2.5 hours, then quenched with 2.13 g of ammonium chloride. The mixture was allowed to warm to ambient temperature and then filtered through Celite. The resulting thick oil was chromatographed on 350 mL silica and eluted with 1:3 ethyl acetate/hexanes to afford a greasy white solid (347 mg, 24%). m.p. 42°–46° C. $^1$H NMR (CDCl$_3$, 300 MHz) δ 0.92 (d, J=6 Hz, 1H), 0.96 (d, J=6 Hz), 1.20 (m, 1H), 1.38 (m, 1H), 1.81 (m, 1H), 3.80 (dt, J=6, 9 Hz, 1H), 4.09 (m, 1H), 4.25 (br t, J=4.5 Hz, 1H), 5.32 (m, 1H), 5.92 (ddd, J=6, 10.5, 18 Hz, 1H). MS (DCI/NH$_3$) m/e 144 (M+H)$^+$.

Example 9B (4S,5R)-2,2-Dimethyl-4-isobutyl-5-vinyl-1,3-dioxolane

To the crude alcohol resulting from Example 9A dissolved in dichloromethane was added p-toluenesulfonic acid (500 mg) and 2,2-dimethoxypropane. The reaction was stirred at ambient temperature for 24 hours and poured into saturated sodium bicarbonate solution. The organic phase was separated, dried over magnesium sulfate and concentrated by distillation to give the title compound. $^1$H NMR (CDCl$_3$, 300 MHz) δ 0.92 (d, J=6 Hz, 3H), 0.96 (d, J=6 Hz, 3H), 1.17 (ddd, J=4.5, 9.0, 15 Hz, 1H), 1.38 (s, 3H), 1.48 (s, 3H), 1.75 (m, 1H), 4.24 (ddd, J=3, 6, 9 Hz, 1H), 4.48 (m, 1H), 5.22 (ddd, J=1, 2, 9 Hz, 1H), 5.27 (ddd, J=1, 2, 17 Hz, 1H), 5.81 (ddd, J=7.5, 9, 17 Hz, 1H).

Example 9C (4S,5R)-2,2-Dimethyl-4-(2-methylpropan-1-yl)-5-formyl-1,3-dioxolane N,N-Dimethylhydrazone A dichloromethane solution of the product of Example 9B (1 g) was cooled to −78° C. and a stream of ozone was passed through the solution until a blue color persisted. Excess ozone was removed with nitrogen ebullition. The crude ozonide was added to zinc dust (530 mg) in 0.5 mL of HOAc. The reaction is allowed to warm to ambient temperature and stirred overnight. Dichloromethane was added and the organic layer was separated. To it was added dimethylhydrazine (490 mg) and excess magnesium sulfate. The reaction was stirred for 3 hours and filtered. The filtrate was concentrated under reduced pressure to give the crude hydrazone. The title compound was obtained following purification by silica gel chromatography; the 300 MHz $^1$H NMR spectrum was found to be identical to that obtained on Example 8B.

EXAMPLE 10

Alternative Preparation of (4S,5R)-2,2-Dimethyl-4-(isobutyl-1-ene)-5-hydroxymethyl-1,3-dioxolane

Example 10A (2S,3R)-2,3-Dihydroxy-5-methyl-4-hexenoic Acid Acetonide

Isopropyltriphenylphosphonium bromide (26.9 g, 69.9 mmol) was ground to a fine powder and suspended in 200 mL of THF (distilled from sodium benzophenone ketyl), then cooled to 4° C. Butyllithium (1.6M in hexanes, 69.9 mmol, 44 mL) was added, then the stirring mixture was allowed to warm to ambient temperature. The known (2S,3R)-2,3,4-trihydroxy-γ- butyrolactone-2,3-acetonide, Hudlicky, T.; Price, J. D.; Synlett. 159 (1990), (4.06 g, 23.3 mmol), dissolved in 100 mL of THF, was added via syringe, and the resulting mixture was heated to reflux for 1 hour, then allowed to cool to ambient temperature while stirring under N$_2$. After stirring overnight at ambient temperature, 600 mL of water was added. The resulting suspension was washed with diethyl ether and then acidified with Amberlite IR-120(plus) resin to a pH of 2–3. The mixture was filtered to remove the resin, and then the filtrate was extracted with methylene chloride. The combined organic extracts were dried over sodium sulfate, filtered, and evaporated to give a yellow foam. This amorphous solid was extracted with boiling ether, which was then evaporated to give a greenish oil (3.17 mg, 68%). $^1$H NMR (CDCl$_3$, 300 MHz) δ 1.43 (s, 3H), 1.63 (s, 3H), 1.76 (d, J=6 Hz, 6H), 4.63 (m, 1H), 5.14 (m, 2H).

Example 10B (4S,5R)-2,2-Dimethyl-4-(isobutyl-1-ene)-5-hydroxymethyl-1,3-dioxolane To the compound resulting from Example 10A (1 equivalent) dissolved in dimethoxyethane is added N-methylmorpholine (1 equivalent). The mixture is cooled to −15° C. and isobutylchloroformate (1 equivalent) is added. After stirring the reaction for 1 minute, sodium borohydride (1.5 equivalents) in water is added. The reaction is stirred at −15° C. for 30 seconds and then worked up to give the title compound.

EXAMPLE 11

Alternative Preparation of (4S,5R)-2,2-Dimethyl-4-(isobutyl-1-ene)-5-formyl-1,3-dioxolane The compound resulting from Example 10A is reacted with methoxymethylamine in the presence of isobutylchloroformate to give the methoxymethylamide. Reduction of this amide using the procedure of Goel et al., Org. Syn. 67, 69–74 (1988) affords the title compound.

EXAMPLE 12

Alternative Preparation of (2S,3R,4S)-2-Amino-1-cyclohexyl-3,4-dihydroxy-6-methylheptane hydrochloride salt The resultant compound from Example 10A (1.0 g, 4.99 mmol) was reacted with cyclohexylmethyllithium (12.5 mmol) in 3:2 pentane/diethyl ether to give 576 mg of the corresponding ketone. $^1$H NMR (CDCl$_3$, 300 MHz) δ 1.40 (s, 3H), 1.63 (s, 3H), 1.72 (s, 6H), 1.83 (m, 1H), 2.24 (dd, J=18, 6 Hz, 1H), 2.41 (dd, J=18, 6 Hz, 1H), 4.5 (d, J=7.5 Hz, 1H), 5.01 (complex d, J=9 Hz, 1H), 5.12 (dd, J=6, 7 Hz, 1H). MS (DCI/NH$_3$) m/e 298 (M+H+NH$_3$)+.

To a solution of the above ketone in pyridine is added hydroxylamine hydrochloride (1.1 mole equivalents). After stirring several hours, the solvent is evaporated and the residue partitioned between ethyl acetate and saturated NaHCO$_3$. Following the usual extractive work-up and drying over sodium sulfate, the filtrate is concentrated under reduced pressure. The residue obtained is hydrogenated (3 atmospheres of hydrogen) 6N hydrochloric acid over PtO$_2$. Removal of the catalyst by filtration, evaporation of the filtrate, and drying provides the title compound.

EXAMPLE 13

Alternative Preparation of (4S,5R)-2,2-Dimethyl-4-isobutyl-5-formyl-1,3-dioxolane

Example 13A (4S,5R)-2,2-Dimethyl-4-isobutyl-5-phenylthiomethyl-1,3-dioxolane The known epoxy alcohol (Smith et al. Tetrahedron Lett. 31, 6329-30 (1990)) is reacted with thiophenol and aqueous sodium hydroxide at elevated temperature according to the procedure of Masamune et al. (J. Am. Chem. Soc. 104, 3515–16 (1982)) to give the phenylthio diol. Protection of the diol using 1 equivalent of p-toluene sulfonic acid and 2,2-dimethoxypropane gives the title compound.

Example 13B (4S,5R)-2,2-Dimethyl-4-isobutyl-5-formyl-1,3-dioxolane

The phenyl sulfide resulting from Example 13A is reacted with 1 equivalent of m-chloroperoxybenzoic acid at −78° C. The resulting sulfoxide is stirred with acetic anhydride and heated to give the Pummerer rearrangement product. Treatment of the acetoxy sulfide with sodium carbonate gives the title compound which is identical to the aldehyde intermediate in the preparation of Example 8B.

EXAMPLE 14

Alternative Preparation of N-Boc-4-Thiazoylalaninyl Amide of (2S,3R,4S) 2-amino-1-cyclohexyl-3,4-dihydroxy-6-methylheptane The crude amine diol hydrochloride salt resulting from Example 8A (12.3 g, 65.3 mmol) using the procedure described in Example 8B and the following reagent quantities: oxalyl chloride (6.3 mL, 72 mmol), DMSO (11.1 mL, 144 mmol), triethylamine (45 mL, 327 mmol), MgSO$_4$ (15.7 g), dimethylhydrazine (20 mL, 261 mmol), t-BuLi (1.7M, 111 mL, 189 mmol), cyclohexylmethyl iodide (22 g, 98 mmol), 2800 Raney nickel (30 g), and 33 mL of 6N HCl, were dissolved in 113 ml DMF. N-Methylmorpholine (10 ml, 91 mmol), the compound resulting from Example 1Q, N-tert-butoxycarbonyl-4-thiazoylalanine, (11.9 mg, 39.7 mmol) and 1-hydroxybenzotriazole hydrate (16.1 g, 119 mmol) were added. The reaction was cooled to −23° C. and 1-ethyl-3-(3-dimethylaminopropyl)carbodiimide hydrochloride (8.4 g, 43.6 mmol) was added. The mixture was stirred under N$_2$ and allowed to warm to ambient temperature over 24 hours. The reaction mixture was partitioned between ethyl acetate and saturated aqueous sodium bicarbonate and the aqueous layer was separated and extracted with ethyl acetate. The combined organic layers were dried over sodium sulfate, filtered, and evaporated. The residue obtained was crystallized from ethyl acetate/hexanes to give 10.25 g. (32% yield from Example 8A). m.p. 154°–157° C. $[α]^{25}_D$= −35.7° (C=1, CHCl$_3$). Anal calcd for C$_{25}$H$_{43}$N$_3$SO$_5$: C, 60.33; H, 8.64; N, 10.29. Found: C, 60.34; H, 8.66; N, 8.40.

EXAMPLE 15

Alternative Preparation of 2(S)-2-Benzyl-3-(1-methylpiperazin-4-ylsulfonyl)propionyl-L-(4-thiazolyl) Ala Amide of (2S,3R,4S)-2-Amino-1-cyclohexyl-3,4-dihydroxy-6-methylheptane

Example 15A (2S,3R,4S)-2-Amino-1-cyclohexyl-3,4-dihydroxy-6-methylheptane

A 3.5% solution of (2S,3R,4S)-2-t-butyloxycarbonylamino-1-cyclohexyl-3,4-dihydroxy-6-methylheptane in 4N ethanolic hydrochloric acid was prepared at 0°–5° C. After 4 hours at 0°–5° C., nitrogen was bubbled through the reaction mixture to remove dissolved hydrochloric acid. The solvent was removed under reduced pressure at 50° C. to afford a solid, which was dissolved in ethyl acetate and water. Potassium carbonate was added to bring the pH of the mixture to between 10 and 11, and the layers were separated. The aqueous layer was extracted with additional portions of ethyl acetate. The combined organic extracts were washed with water and brine, dried over magnesium sulfate, and concentrated under reduced pressure at 50° C. to afford a solid. The solid was crystallized by dissolving in a minimum amount of ethanol at 40° C. and then water was slowly added until the ratio of ethanol to water was 40/60 (w/w). The solution was cooled to 0°–5° C. for 2 hours and the product was collected by filtration. The solid was then dried under vacuum at 45° C. to provide the title compound as a white crystalline solid (65–72%). m.p. 106°–108° C. MS (DCI/NH$_3$) m/e 244 (M+H)+.

Example 15B

Boc-L-(4-Thiazolyl)-Ala Amide of (2S,3R,4S)-2-Amino-1-cyclohexyl-3,4-dihydroxy-6-methylheptane To a solution of the product of Example 15A (14.25 g, 58.5 mmol), N-Boc-L-4-thiazolyl-alanine (17.45 g, 64.4 mmol), and 1-hydroxybenzotriazole hydrate (HOBT) (9.86 g, 64.4 mmol) dissolved in dimethylformamide (DMF) (33 mL) and cooled to 0°–5° C. in an ice bath was added dropwise over 30 minutes a solution of 1,3-dicyclohexylcarbodiimide (DCC) (14.5 g, 70.3 mmol) dissolved in DMF (27 mL). After one hour, the reaction mixture was allowed to warm to ambient temperature and stirred for 24 hours. The reaction was quenched by the addition of citric acid (1.14 g, 6.0 mmol) and ethanol (1.31 mL, 1.05 g, 22.0 mmol). The mixture was stirred for 1 hour and then ethyl acetate was added (285 mL). After an additional 30 minutes, the solid by-product was removed by filtration and washed with ethyl acetate (48 mL). Additional ethyl acetate (1.9 L) was added and the organic phase was washed with 1% sodium chloride (713 mL), 5% citric acid containing 1% sodium chloride (2×713 mL), 8% sodium bicarbonate (2×713 mL) and 20% sodium chloride (2×713 mL) and concentrated under reduced pressure to afford an off-white solid. The solid was dissolved in isopropanol (200 mL) with warming, treated with decolorizing carbon at 50° C. for one hour, and filtered through Celite. The filtrate was diluted with isopropanol (50 mL) and stirred at ambient temperature with a mechanical stirrer for 15 hours. The solid suspension was cooled to 0°–5° C. with an ice bath and stirred at this temperature for 3 hours. The solid was removed by cold filtration, washed with cold 1:1 isopropanol/heptane (100 mL), and dried in a vacuum oven at 50° C. for 48 hours to afford the title compound as a white solid in 85% yield. m.p. 156°–158° C. MS (DCI/NH$_3$) m/e 498 (M+H)$^+$.

Example 15C

H-L-(4-Thiazolyl)Ala Amide of (2S,3R,4S)-2-Amino-1-cyclohexyl-3,4-dihydroxy-6-methylheptane A 12% solution of the product of Example 15B at 15°–25° C. in 3N aqueous hydrochloric acid was prepared. After 4 hours at 15°–25° C., the reaction mixture was quenched by pouring it into a mixture of 4% sodium hydroxide/15% sodium chloride/ethyl acetate. The pH of the mixture was brought up to 10–12 by the addition of 10% sodium hydroxide. The layers were separated and the aqueous layer extracted with ethyl acetate (2×). The combined organic extracts were washed with 25% sodium chloride (2×), dried over magnesium sulfate, treated with activated carbon at 50° C. for 1 hour, and filtered through Celite. The filtrate was concentrated to a solid under reduced pressure at 45° C. The solid was crystallized by dissolving in a minimum amount of ethyl acetate (5× by weight) and triturating with heptane until the ratio of ethyl acetate to heptane was 30/70 (w/w). The solution was cooled to 0–5° C. and stirred for two hours and then filtered. The solid was dried in a vacuum oven at 45° C. for 60 hours or until the loss on dryng was less than 0.1%. The title compound was obtained as a white crystalline solid in 70–82% yield. m.p. 109°–112° C. MS (DCI/NH$_3$) m/e 398 (M+H)$^+$.

Example 15D (2S)-2-Benzyl-3-(1-methylpiperazin-4-yl sulfonyl) propionyl-L-(4-Thiazolyl) Ala Amide of (2S,3R,4S)-2-Amino-1-cyclohexyl-3,4-dihydroxy-6-methylheptane The product of Example 15C (3.00 g, 7.6 mmol), the product of Example 6C, 2S-benzyl-3-(1-methylpiperazin-4-yl sulfonyl)propionic acid, (2.59 g, 7.9 mmol), and HOBT (1.27 g, 8.3 mmol) were dissolved in DMF (30 mL). After stirring at ambient temperature for 1 hour, the reaction mixture was cooled to 0°–5° C. in an ice bath and treated with the dropwise addition over a 30 minute period of a solution of DCC (1.72 g, 8.3 mmol) dissolved in DMF (8 mL). After 1 hour, the reaction mixture was allowed to warm to ambient temperature and stirred for 24 hours. The reaction mixture was quenched with citric acid (0.15 g, 0.26 mmol) and ethanol (0.17 mL, 3.04 mmol) and stirred for 1 hour. Ethyl acetate (60 mL) was added and the mixture was stirred for an additional hour. The by-product was removed by filtration and washed with ethyl acetate (10 mL). The filtrate was diluted with ethyl acetate (400 mL) and washed with 5% sodium bicarbonate solution (2×100 mL), 1% sodium chloride solution (100 mL), and 20% sodium chloride solution (100 mL). The solvent was removed under reduced pressure to afford an off-white solid. The solid was dissolved in isopropanol (80 mL) with warming, treated with decolorizing carbon at 55° C. for 1 hour, filtered through Celite, and stirred at ambient temperature with a mechanical stirrer for 12 hours. The white solid suspension was cooled to 0°–5° C. in an ice bath for 3 hours and filtered cold. The solid obtained was washed with cold 1:1 heptane/isopropanol (25 mL) and dried in a vacuum oven at 55° C. for 48 hours to afford the title comound (4.32 g, 81%) as a white solid. m.p. 169°–170° C. MS (DCI/NH$_3$) m/e 706 (M+H)$^+$.

EXAMPLE 16

Alternative Preparation Of

Diethyl (4-thiazolylmethyl)acetamidomalonate

4-Chloromethylthiazole hydrochloride (184.6 g, 0.89 mole) was dissolved in 700 ml of water and the resulting solution cooled to 5° C. The solution was then made basic with concentrated ammonium hydroxide to a final pH of 11 and then extracted. The combined organic extracts were dried over magnesium sulfate, filtered, and concentrated in vacuo to give 4-chloromethylthiazole which was used immediately as outlined below.

To an oven-dried 2 liter 3-neck round bottom flask equipped with a mechanical stirrer, relux condenser and nitrogen inlet containing 500 mL of absolute ethanol was added sodium (19.8 g, 0.86 mole). This mixture was allowed to reflux until complete dissolution of the sodium metal. The resultant solution of sodium ethoxide was cooled to approximately 40° C. and diethyl acetamidomalonate (186.1 g, 0.86 mole) was added. The resultant mixture was refluxed for 30 minutes, then cooled to about 50° C. and treated with potassium iodide (2.0 g) and dimethylformamide (2 ml). A freshly prepared solution of 4-chloromethylthiazole (0.89 mole) in 200 mL of absolute ethanol was added dropwise over a period of 20 minutes and the mixture was maintained at 50 ° C. for 24 hours. The mixture was then cooled in an ice bath, diluted with ethyl acetate and filtered through a pad of Celite. Concentration and drying gave 265 g of the desired product as light yellow crystals. m.p. 104°–106° C.

EXAMPLE 17

Alternative Preparation of (2S,3R,4S)-2-Amino-1-cyclohexyl-3,4-dihydroxy-6-methylheptane (2S,3R,4S)-2-[(tert-Butyloxycarbonyl)amino]-1-cyclohexyl-3,4-dihydroxy-6-methylheptane was prepared as described in the literature: Luly, J. R.; Hsiao, C. N.; BaMaung, N.; Plattner, J. J. J. Org. Chem. 53, 6109 (1988). This compound (413 mg, 1.2 mmol) was dissolved in 4N HCl in dioxane (6 mL) and stirred at ambient temperature for 1 hour and then concentrated in vacuo to give the hydrochloride salt, which was dissolved in tetrahydrofuran (2 mL) and treated with 1N sodium hydroxide to pH 12. The mixture was extracted with methylene chloride (5×5 mL). The combined organic extracts were dried over potassium carbonate and concentrated in vacuo to afford the title compound (294 mg, 99%). The 300 MHz $^1$H NMR spectrum was found to be consistent with the proposed structure.

EXAMPLE 18

Alternative Preparation of (2S,3R,4S)-2-Amino-1-cyclohexyl-3,4-dihydroxy-6-methylheptane

Example 18A (2R,3S)-1-Benzyl-2,3-(isopropylidenedioxy)cyclohexa-4,6-diene

The title compound is prepared by the microbial oxidation of diphenylmethane by *Pseudomonas putida* 39D followed by diol protection as the acetonide using the method of T. Hudlicky et al. J. Am. Chem. Soc. 110, 4735–41 (1988).

Example 18B (3R,4S)-3,4-(Isopropylidenedioxy)-6-methyl-1-phenylhept-5-en-2-one Oxidative cleavage of the compound resulting from Example 18A using the procedure of Hudlicky et al. J. Am. Chem. Soc. 110, 4735–41 (1988) and D. Gibson et al. Biochemistry, 9, 1626–30 (1970) provides the crude keto aldehyde. Wittig olefination using the ylide derived from isopropyltriphenylphosphonium bromide provides the title compound.

Example 18C (2S,3R,4S)-2-Amino-1-cyclohexyl-3,4-dihydroxy-6-methylheptane

To a solution of the resultant compound of Example 18B in pyridine is added hydroxylamine hydrochloride (1.1 molar equivalents). After stirring several hours, the solvent is evaporated and the residue partitioned between ethyl acetate and saturated NaHCO$_3$. Following usual extractive work-up and drying over sodium sulfate, the filtrate is concentrated in vacuo. The residue obtained is hydrogenated at 3 atmospheres of hydrogen in 6N hydrochloric acid over PtO$_2$. The catalyst is removed by filtration; evaporation and drying over sodium sulfate of the filtrate provides the title compound.

EXAMPLE 19

Alternative Preparation of (2S,3R,4S)-2-Amino-1-cyclohexyl-3,4-dihydroxy-6-methylheptane

Example 19A (2R,3S)-1-(Cyclohexylmethyl)-2,3 (isopropylidenedioxy)-cyclohexa-4,6-diene The title compound is prepared by the microbial oxidation of cyclohexylmethylbenzene (W. Korte et al. J. Org. Chem. 39, 1168–70 (1974)) by *Pseudomonas putida* 39D using the method of T. Hudlicky et al. J. Am. Chem. Soc. 110, 4735–41 (1988) and D. Gibson et al. Biochemistry, 9, 1626–30 (1970) followed by protection as the acetonide using 2,2-dimethoxypropane and p-toluenesulfonic acid.

Example 19B (3R,4S)-1-Cyclohexyl-3,4-(isopropylidenedioxy)-6-methylhept-5-en-2-one Oxidative cleavage of the diene resulting from Example 19A using the procedure of T. Hudlicky et al. J. Am. Chem. Soc. 110, 4735–41 (1988) provides the crude keto aldehyde. Wittig olefination by the ylide derived from isopropyltriphenylphosphonium bromide provides the title compound.

Example 19C (2S,3R,4S)-2-Amino-1-cyclohexyl-3,4-dihydroxy-6-methylheptane

The compound resulting from Example 19B is treated by the procedures described in Example 18C to give the title compound.

EXAMPLE 20

Alternative Preparation of (2S,3R,4S)-2-Amino-1-cyclohexyl-3,4-dihydroxy-6-methylheptane

Example 20A (2R,3S)-1-Benzyl-2,3-diacetoxycyclohexa-4,6-diene

The title compound is prepared by the microbial oxidation of diphenylmethane by *Pseudomonas putida* 39D using the method of T. Hudlicky et al. J. Am. Chem. Soc. 110, 4735–41 (1988) and D. Gibson et al. Biochemistry, 9, 1626–30 (1970) followed by protection as the diacetate using acetic anhydride in pyridine.

Example 20B (3R,4S)-3,4-Diacetoxy-6-methyl-1-phenylhept-5-en-2-one

Oxidative cleavage of the compound resulting from Example 20A using the procedure of T. Hudlicky et al. J. Am. Chem. Soc. 110, 4735–41 (1988) provides the crude keto aldehyde. Wittig olefination by the ylide derived from isopropyltriphenylphosphonium bromide provides the title compound.

Example 20C (2S,3R,4S)-2-Amino-1-cyclohexyl-3,4-dihydroxy-6-methylheptane

To a solution of the resultant compound from Example 20B in pyridine is added hydroxylamine hydrochloride (1.1 molar equivalents). After the reaction is complete, the solvent is removed in vacuo and the residue obtained is partitioned between ethyl acetate and saturated NaHCO$_3$. After the usual extractive work-up and drying over sodium sulfate, the filtrate is concentrated in vacuo and the residue obtained hydrogenated under 3 atmospheres of hydrogen in acetic acid over PtO$_2$. The catalyst is removed by filtration; evaporation and drying over sodium sulfate of the filtrate provides the the amino diacetate. The diacetate is dissolved in methanol and stirred with potassium carbonate. The solids are removed by filtration; concentration of the filtrate gives the title compound.

EXAMPLE 21

Alternative Preparation of (2S,3R,4S)-2-Amino-1-cyclohexyl-3,4-dihydroxy-6-methylheptane

Example 21A (2R,3S)-1-(Cyclohexylmethyl)-2,3-diacetoxycyclohexa-4,6-diene

The title compound is prepared by the microbial oxidation of cyclohexylmethylbenzene (W. Korte et al. J. Org. Chem. 39, 1168–70 (1974)) by *Pseudomonas putida* 39D using the method of T. Hudlicky et al. J. Am. Chem. Soc. 110, 4735–41 (1988) and D. Gibson et al. Biochemistry, 9, 1626–30 (1970) followed by protection as the diacetate using acetic anhydride in pyridine.

Example 21B (3R,4S)-1-Cyclohexyl-3,4-diacetoxy-6-methylhept-5-en-2-one

Oxidative cleavage of the compound resulting from Example 21A using the procedure of T. Hudlicky et al. J. Am. Chem. Soc. 110, 4735–41 (1988) provides the crude keto aldehyde. Wittig olefination by the ylide derived from isopropyltriphenylphosphonium bromide provides the title compound.

Example 21C (2S,3R,4S)-2-Amino-1-cyclohexyl-3,4-dihydroxy-6-methylheptane

The compound resulting from Example 21B is treated by the procedures described in Example 20C to provide the title compound.

The foregoing is merely illustrative of the invention and is not intended to limit the invention to the disclosed processes. Variations and changes which are obvious to one skilled in the art are intended to be within the scope and nature of the invention which are defined in the appended claims.

What is claimed is:

1. A process for the preparation of a substantially pure compound of the formula:

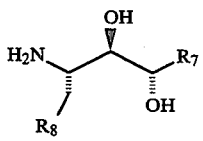

wherein $R_7$ is loweralkyl having 2 to 7 carbon atoms and $R_8$ is loweralkyl, $C_3$-$C_7$ cycloalkyl or aryl wherein aryl is phenyl, naphthyl, tetrahydronaphthyl or indanyl wherein the aryl group is unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or an acid addition salt thereof, comprising:

(a) hydrogenating a compound of the formula:

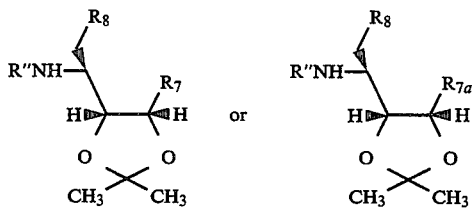

wherein $R_7$ is loweralkyl having 2 to 7 carbon atoms, $R_{7a}$ is $-CH=C(R_{7a1})(R_{7a2})$ wherein $R_{7a1}$ and $R_{7a2}$ are independently selected from hydrogen and loweralkyl, $R_8$ is loweralkyl, $C_3$-$C_7$ cycloalkyl or aryl as defined above and $R''$ is benzyl, substituted benzyl wherein the phenyl ring of the benzyl group is substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or $(R''')_2N-$ wherein $R'''$ is loweralkyl and (b) removing the acetonide protecting group.

2. A process for the preparation of a substantially pure compound of the formula:

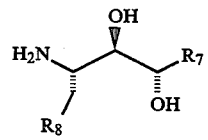

wherein $R_7$ is loweralkyl having 2 to 7 carbon atoms and $R_8$ is loweralkyl, $C_3$-$C_7$ cycloalkyl or aryl wherein aryl is phenyl, naphthyl, tetrahydronaphthyl or indanyl wherein the aryl group is unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or an acid addition salt thereof, comprising:

(a) reacting a compound of the formula:

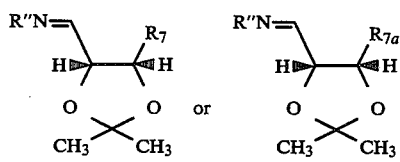

wherein $R_7$ is loweralkyl having 2 to 7 carbon atoms, $R_{7a}$ is $-CH=C(R_{7a1})(R_{7a2})$ wherein $R_{7a1}$ and $R_{7a2}$ are independently selected from hydrogen and loweralkyl and $R''$ is benzyl, substituted benzyl wherein the phenyl ring of the benzyl group is substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or $(R''')_2N-$ wherein $R'''$ is loweralkyl with an organometallic reagent of the formula $R_8CH_2M$ wherein M is lithium or a magnesium halide and $R_8$ is loweralkyl, $C_3$-$C_7$ cycloalkyl or aryl as defined above to give a compound of the formula:

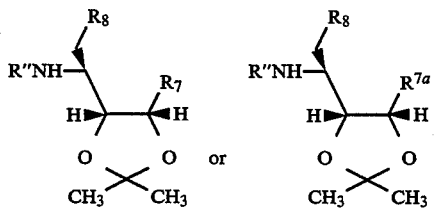

(b) hydrogenating the product of step (a) and
(c) removing the acetonide protecting group.

3. A process for the preparation of a substantially pure compound of the formula:

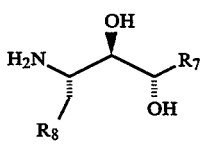

wherein R$_7$ is loweralkyl having 2 to 7 carbon atoms and R$_8$ is loweralkyl, C$_3$-C$_7$ cycloalkyl or aryl wherein aryl is phenyl, naphthyl, tetrahydronaphthyl or indanyl wherein the aryl group is unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or an acid addition salt thereof, comprising:

(a) reacting a compound of the formula:

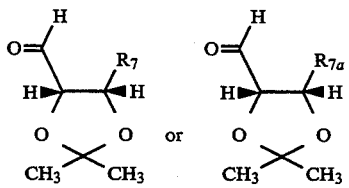

wherein R$_7$ is loweralkyl having 2 to 7 carbon atoms and R$_{7a}$ is —CH═C(R$_{7a1}$)(R$_{7a2}$) wherein R$_{7a1}$ and R$_{7a2}$ are independently selected from hydrogen and loweralkyl with R"NH$_2$ wherein R" is benzyl, substituted benzyl wherein the phenyl ring of the benzyl group is substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide; or (R''')$_2$N— wherein R''' is loweralkyl to give a compound of the formula:

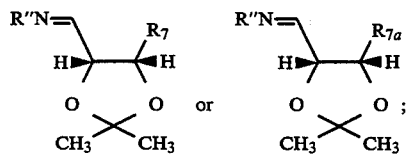

(b) reacting the product of step (a) with an organometallic reagent of the formula R$_8$CH$_2$M wherein M is lithium or a magnesium halide and R$_8$ is loweralkyl, C$_3$-C$_7$ cycloalkyl or aryl as defined above to give a compound of the formula:

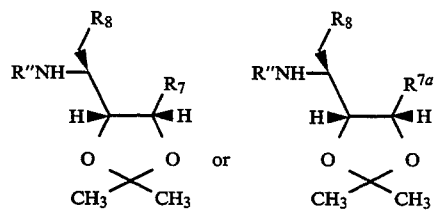

(c) hydrogenating the product of step (b) and
(d) removing the acetonide protecting group.

4. The process of claim 1 wherein R" is benzyl or (CH$_3$)$_2$N—, R$_7$ is isobutyl, R$_{7a}$ is —CH═C(CH$_3$)$_2$ and R$_8$ is cyclohexyl.

5. The process of claim 2 wherein R" is benzyl or (CH$_3$)$_2$N—, R$_7$ is isobutyl, R$_{7a}$ is —CH═C(CH$_3$)$_2$ and R$_8$ is cyclohexyl.

6. The process of claim 3 wherein R" is benzyl or (CH$_3$)$_2$N—, R$_7$ is isobutyl, R$_{7a}$ is —CH═C(CH$_3$)$_2$ and R$_8$ is cyclohexyl.

7. A process for the preparation of a substantially pure compound of the formula:

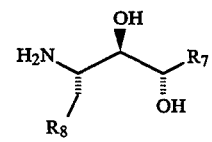

wherein R$_7$ is isobutyl and R$_8$ is cyclohexyl; or an acid addition salt thereof, comprising:

(a) hydrogenating a compound of the formula:

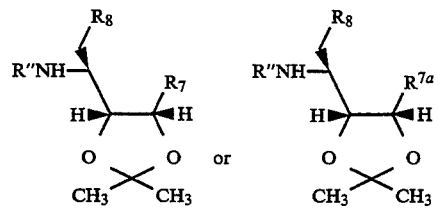

wherein R$_7$ is isobutyl, R$_{7a}$ is —CH═C(CH$_3$)$_2$, R$_8$ is cyclohexyl and R" is benzyl or (CH$_3$)$_2$N— and
(b) removing the acetonide protecting group.

8. A process for the preparation of a substantially pure compound of the formula:

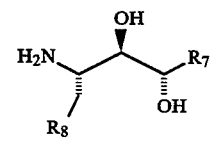

wherein R$_7$ is isobutyl and R$_8$ is cyclohexyl; or an acid addition salt thereof, comprising:

(a) reacting a compound of the formula:

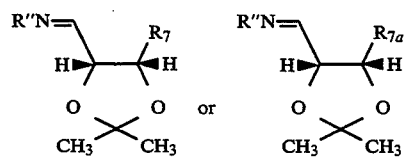

wherein $R_7$ is isobutyl, $R_{7a}$ is —CH=C(CH$_3$)$_2$ and R″ is benzyl or (CH$_3$)$_2$N— with an organometallic reagent of the formula $R_8CH_2M$ wherein M is lithium or a magnesium halide and $R_8$ is cyclohexyl to give a compound of the formula:

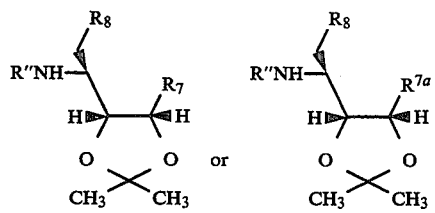

wherein $R_7$, $R_{7a}$, $R_8$ and R″ are defined as above;

(b) hydrogenating the product of step (a) and (c) removing the acetonide protecting group.

9. A process for the preparation of a substantially pure compound of the formula:

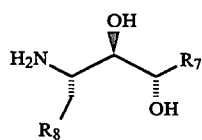

wherein $R_7$ is isobutyl and $R_8$ is cyclohexyl; or an acid addition salt thereof, comprising:

(a) reacting a compound of the formula:

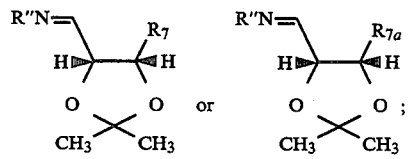

wherein $R_7$ is isobutyl and $R_{7a}$ is —CH=C(CH$_3$)$_2$ with R″NH$_2$ wherein R″ is benzyl or (CH$_3$)$_2$N— to give a compound of the formula:

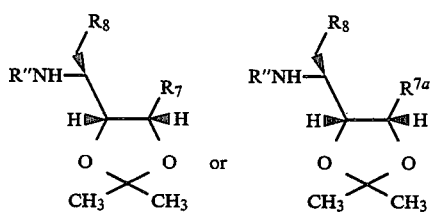

wherein $R_7$, $R_{7a}$ and R″ are defined as above;

(b) reacting the product of step (a) with an organometallic reagent of the formula $R_8CH_2M$ wherein M is lithium or a magnesium halide and $R_8$ is cyclohexyl to give a compound of the formula:

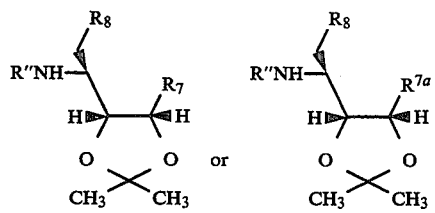

wherein $R_7$ is isobutyl, $R_{7a}$ is —CH=C(CH$_3$)$_2$, $R_8$ is cyclohexyl and R″ is benzyl or (CH$_3$)$_2$N—;

(c) hydrogenating the product of step (b) and (d) removing the acetonide protecting group.

* * * * *